(12) United States Patent
Wilson

(10) Patent No.: US 10,092,734 B2
(45) Date of Patent: *Oct. 9, 2018

(54) METHOD AND TOOLS FOR IMPLANTED DEVICE

(71) Applicant: INTEGRA LIFESCIENCES SWITZERLAND SÄRL, Le Locle (CH)

(72) Inventor: Stephen F. Wilson, North Easton, MA (US)

(73) Assignee: Integra Lifesciences Switzerland SARL, Le Locle (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/387,926

(22) Filed: Dec. 22, 2016

(65) Prior Publication Data

US 2017/0095650 A1 Apr. 6, 2017

Related U.S. Application Data

(60) Division of application No. 14/725,240, filed on May 29, 2015, now abandoned, which is a division of
(Continued)

(51) Int. Cl.
*A61M 27/00* (2006.01)
*F16K 15/04* (2006.01)
*F16K 31/08* (2006.01)
*F16K 35/16* (2006.01)
*F16K 37/00* (2006.01)

(52) U.S. Cl.
CPC ......... *A61M 27/006* (2013.01); *F16K 15/046* (2013.01); *F16K 31/088* (2013.01); *F16K 35/16* (2013.01); *F16K 37/0058* (2013.01)

(58) Field of Classification Search
CPC .. A61M 27/006; F16K 37/0058; F16K 35/16; F16K 15/046; F16K 31/088
See application file for complete search history.

(56) References Cited

U.S. PATENT DOCUMENTS 4,551,128 A 11/1985 Hakim
4,595,390 A 6/1986 Hakim
(Continued)

FOREIGN PATENT DOCUMENTS

EP 421557 A2 4/1991
EP 688575 A1 12/1995
(Continued)

OTHER PUBLICATIONS

Christoph Miethke GMBH & Co. KG, Meithke proGAV® Programmable Shunt System brochure, pp. 3-22; www.miethke.com; AESCULAP AG & Co. KG, Germany; www.aesculap.de.
(Continued)

*Primary Examiner* — Eric Keasel
(74) *Attorney, Agent, or Firm* — Troutman Sanders LLP

(57) ABSTRACT

A method and toolset capable of remotely moving a rotor of an implanted device in a first arcuate direction and detecting a first limit of travel, moving the rotor in a second, opposite direction and detecting a second limit of travel without altering the current performance setting of the implanted device, comparing the first and second limits of travel with known values for a plurality of selectable performance settings, and indicating the current performance setting of the implanted device.

10 Claims, 24 Drawing Sheets

Related U.S. Application Data application No. 13/929,998, filed on Jun. 28, 2013, now Pat. No. 9,149,615, which is a continuation-in-part of application No. 13/705,009, filed on Dec. 4, 2012, now Pat. No. 8,617,142, which is a division of application No. 12/858,193, filed on Aug. 17, 2010, now Pat. No. 8,322,365.

(56) References Cited

U.S. PATENT DOCUMENTS

| | | |
|---|---|---|
| 4,608,992 A | 9/1986 | Hakim |
| 4,615,691 A | 10/1986 | Hakim |
| 4,676,772 A | 6/1987 | Hooven |
| 4,772,257 A | 9/1988 | Hakim |
| 4,885,002 A | 12/1989 | Watanabe |
| 5,263,964 A | 11/1993 | Purdy |
| 5,637,083 A | 6/1997 | Bertrand |
| 5,643,194 A | 7/1997 | Negre |
| 5,667,504 A | 9/1997 | Baumann |
| 5,879,297 A | 3/1999 | Haynor |
| 5,928,182 A | 7/1999 | Kraus |
| 6,009,878 A | 1/2000 | Weijand |
| 6,050,969 A | 4/2000 | Kraus |
| 6,074,394 A | 6/2000 | Krause |
| 6,216,028 B1 | 4/2001 | Haynor |
| 6,305,381 B1 | 10/2001 | Weijand |
| 6,439,538 B1 | 8/2002 | Ito |
| 6,474,360 B1 | 11/2002 | Ito |
| 6,485,449 B2 | 11/2002 | Ito |
| 6,503,249 B1 | 1/2003 | Krause |
| 6,585,677 B2 | 7/2003 | Cowan, Jr. |
| 6,684,904 B2 | 2/2004 | Ito |
| 6,685,638 B1 | 2/2004 | Taylor |
| 6,702,249 B2 | 3/2004 | Ito |
| 6,761,718 B2 | 7/2004 | Madsen |
| 6,840,917 B2 | 1/2005 | Marion |
| 6,883,241 B2 | 4/2005 | Moskowitz |
| 6,926,691 B2 | 8/2005 | Miethke |
| 6,932,787 B2 | 8/2005 | Cowan |
| 6,951,059 B2 | 10/2005 | Moskowitz |
| 6,988,009 B2 | 1/2006 | Grimm |
| 7,197,354 B2 | 3/2007 | Sobe |
| 7,297,246 B2 | 11/2007 | Patel |
| 7,334,582 B2 | 2/2008 | Bertrand |
| 7,334,594 B2 | 2/2008 | Ludin |
| 7,367,968 B2 | 5/2008 | Rosenberg |
| 7,390,310 B2 | 6/2008 | McCusker |
| 7,422,566 B2 | 9/2008 | Miethke |
| 7,658,196 B2 | 2/2010 | Ferreri |
| 7,774,069 B2 | 8/2010 | Olson |
| 7,775,215 B2 | 8/2010 | Hassler, Jr. |
| 7,806,122 B2 | 10/2010 | Hoendervoogt |
| 7,842,004 B2 | 11/2010 | Kassem |
| 7,856,987 B2 | 12/2010 | Bertrand |
| 7,921,571 B2 | 4/2011 | Moureaux |
| 8,015,977 B2 | 9/2011 | Bertrand |
| 8,024,047 B2 | 9/2011 | Olson |
| 8,038,641 B2 | 10/2011 | Soares |
| 8,123,714 B2 | 2/2012 | Ludin |
| 8,322,365 B2 | 12/2012 | Wilson |
| 2002/0022793 A1 | 2/2002 | Bertrand |
| 2004/0010219 A1 | 1/2004 | McCusker |
| 2004/0147906 A1 | 7/2004 | Voyiazis |
| 2004/0162545 A1 | 8/2004 | Brown |
| 2005/0004460 A1 | 1/2005 | Taylor |
| 2005/0022403 A1 | 2/2005 | Moskowitz |
| 2005/0049578 A1 | 3/2005 | Tu |
| 2005/0055009 A1 | 3/2005 | Rosenberg |
| 2005/0092335 A1 | 5/2005 | Bertrand |
| 2005/0096579 A1 | 5/2005 | Bertrand |
| 2005/0096582 A1 | 5/2005 | Burnett |
| 2005/0120571 A1 | 6/2005 | Moskowitz |
| 2005/0187515 A1 | 8/2005 | Varrichio |
| 2006/0009780 A1 | 1/2006 | Foley |
| 2006/0241545 A1 | 10/2006 | Madsen |
| 2007/0093741 A1 | 4/2007 | Miethke |
| 2008/0125690 A1 | 5/2008 | Delaporte |
| 2008/0127689 A1 | 6/2008 | McCusker |
| 2008/0154215 A1 | 6/2008 | Rosenberg |
| 2008/0221436 A1 | 9/2008 | Bertrand |
| 2008/0234638 A1 | 9/2008 | Antonio |
| 2009/0099572 A1 | 4/2009 | Geist |
| 2010/0010338 A1 | 1/2010 | van Dam |
| 2010/0152566 A1 | 6/2010 | Rains |
| 2010/0199506 A1 | 8/2010 | Moureaux |
| 2011/0105991 A1 | 5/2011 | Roth |
| 2011/0105992 A1 | 5/2011 | Girardin |
| 2011/0105993 A1 | 5/2011 | Girardin |
| 2011/0105994 A1 | 5/2011 | Ginggen |
| 2011/0112460 A1 | 5/2011 | Murphy |
| 2011/0118589 A1 | 5/2011 | Negre |
| 2012/0004538 A1 | 1/2012 | Bertrand |

FOREIGN PATENT DOCUMENTS

| | | |
|---|---|---|
| EP | 1159922 A2 | 12/2001 |
| EP | 1243826 A2 | 9/2002 |
| EP | 1604703 A1 | 12/2005 |
| EP | 2236169 A1 | 10/2010 |
| EP | 2420284 A2 | 2/2012 |
| JP | 2006014936 A | 1/2006 |
| WO | WO 2000072781 A2 | 12/2000 |

OTHER PUBLICATIONS

Codman & Shurtleff, Inc., Codman® Hakim® Progammable Valve System for Hydrocephalus; 2006; pp. 1-6; Codman & Shurtleff, Inc., Raynham, MA; www.codman.com.

Codman & Shurtleff, Inc., Codman® Hakim® Progammable Valves brochure; 2004-2009 Revised Oct. 2009, pp. 1-90 with index; Codman & Shurtleff, Inc., Raynham, MA; Codman A division of Johnson & Johnson Medical Ltd. Wokingham, UK; www.codman.com.

Medtronic, Inc., PS Medical® Strata™ Valve Adjustment Kit brochure; pp. 3-9.

Sophysa SA; Instructions for use POLARIS® Valve Adjustment Kit Percutaneous adjustment kit for the Polaris® valve brochure; Jan. 2004; pp. 1-11; Sophysa SA France; contact@sophysa.com.

Sophysa SA; Polaris® The first MRI-stable adjustable valve brochure; May 2009; Sophysa SA France; contact@sophysa.com.

Sophysa SA; The Sophy® Adjustable Pressure Valves brochure; Feb. 2005; Sophysa SA France; contact@sophysa.com.

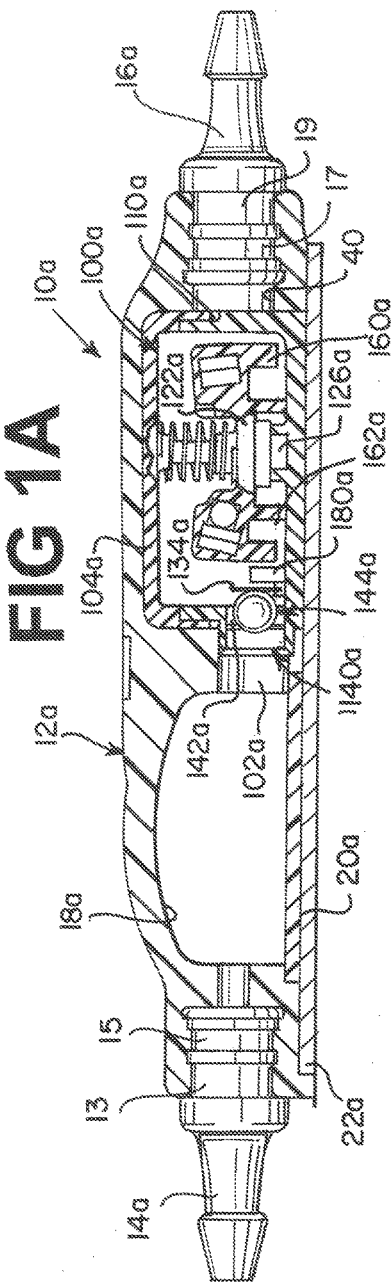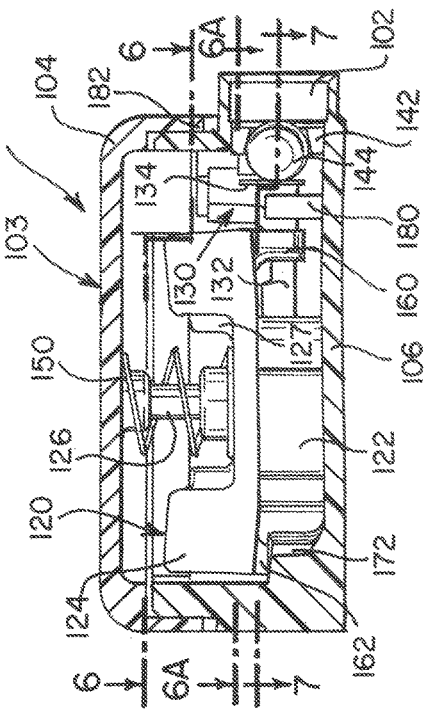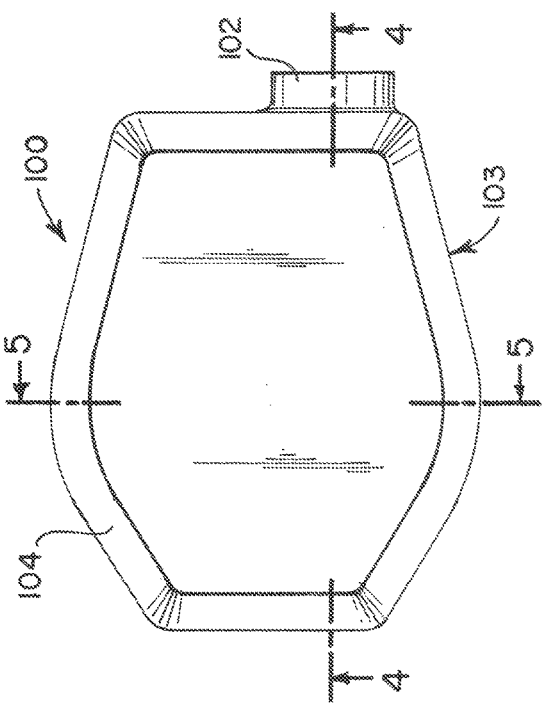

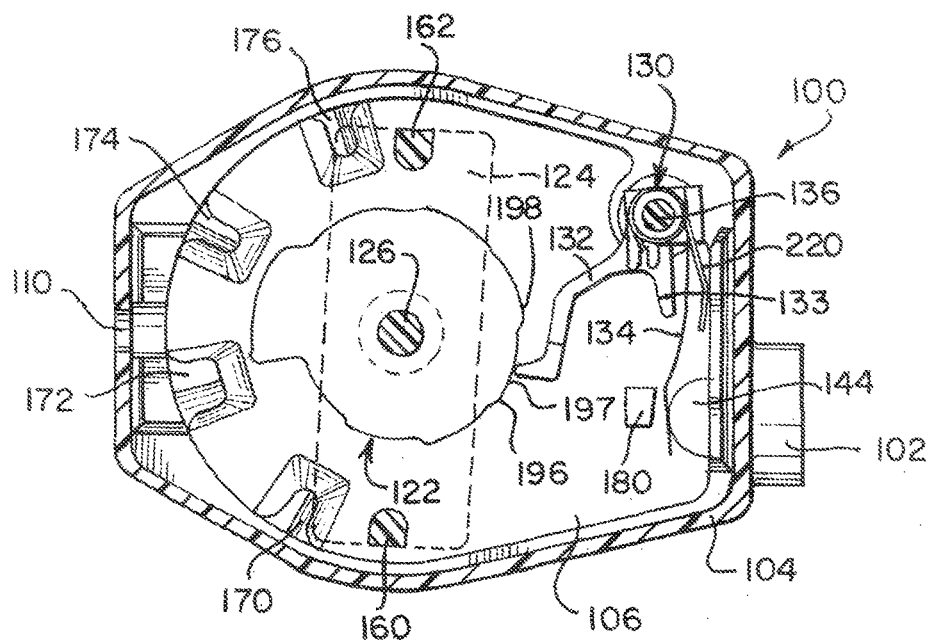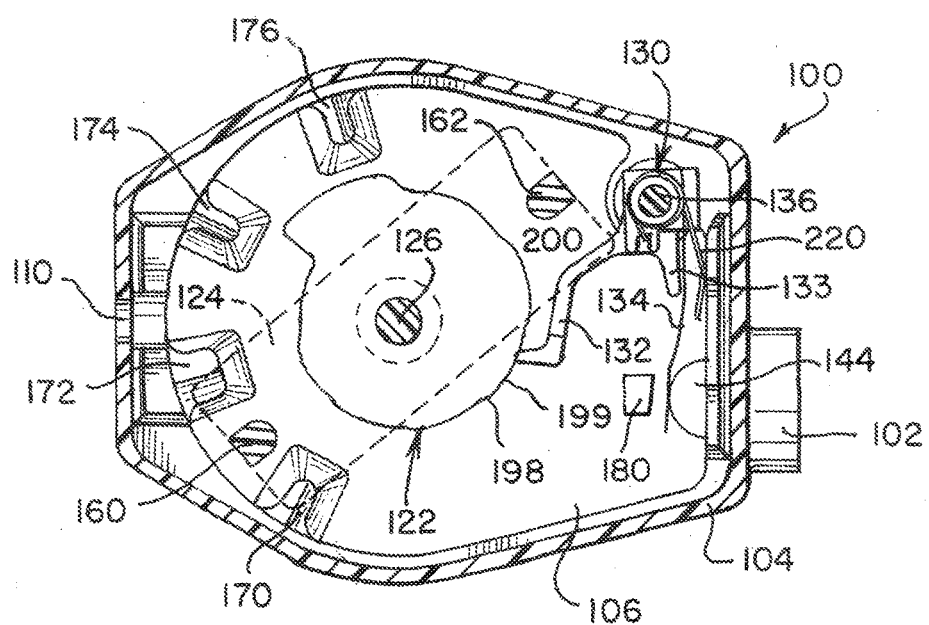

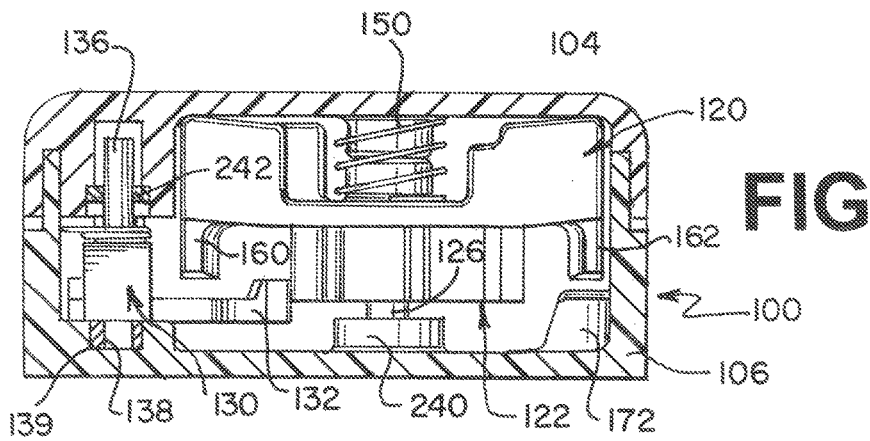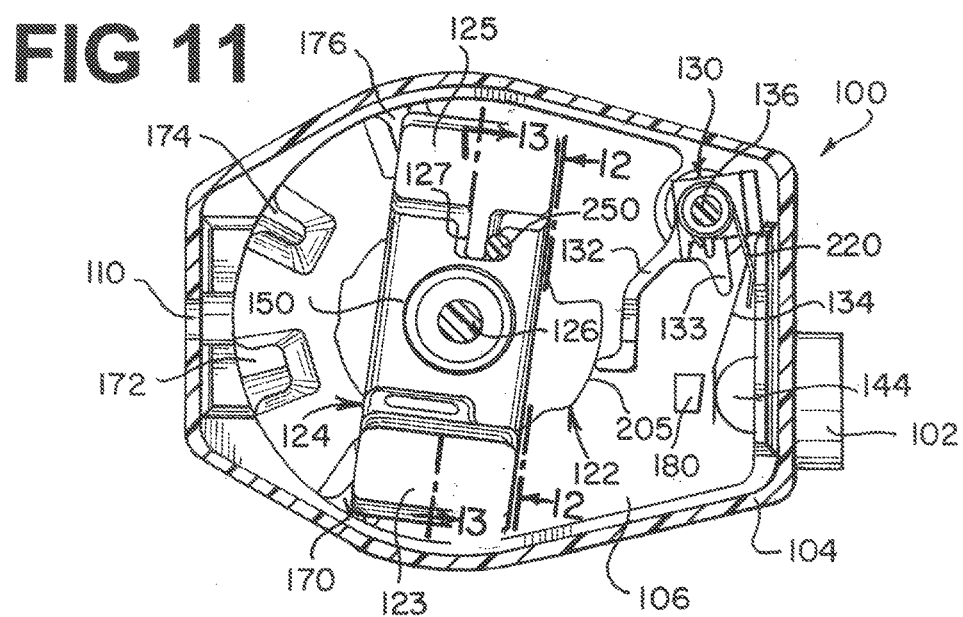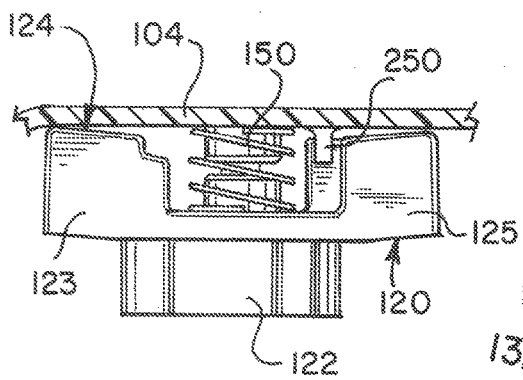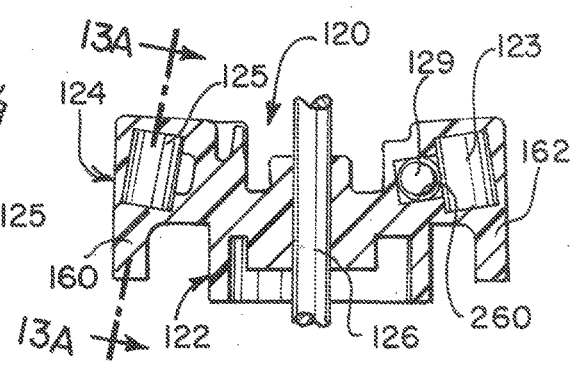

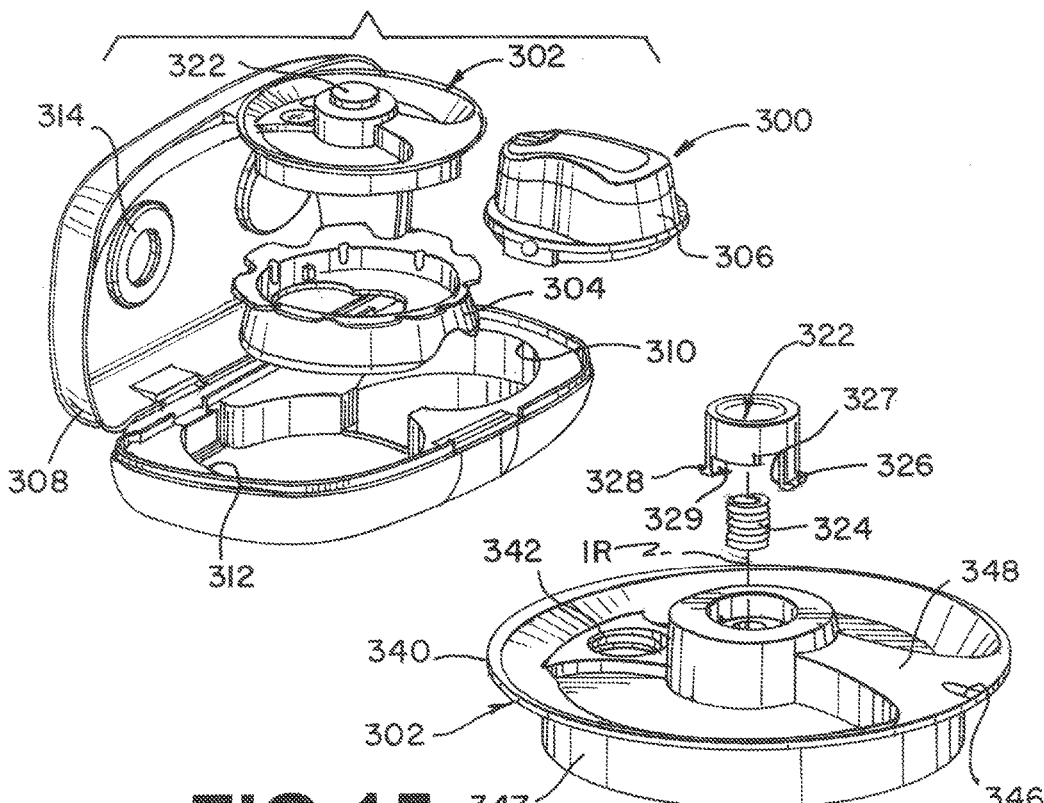
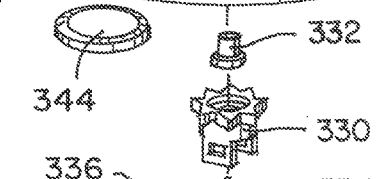
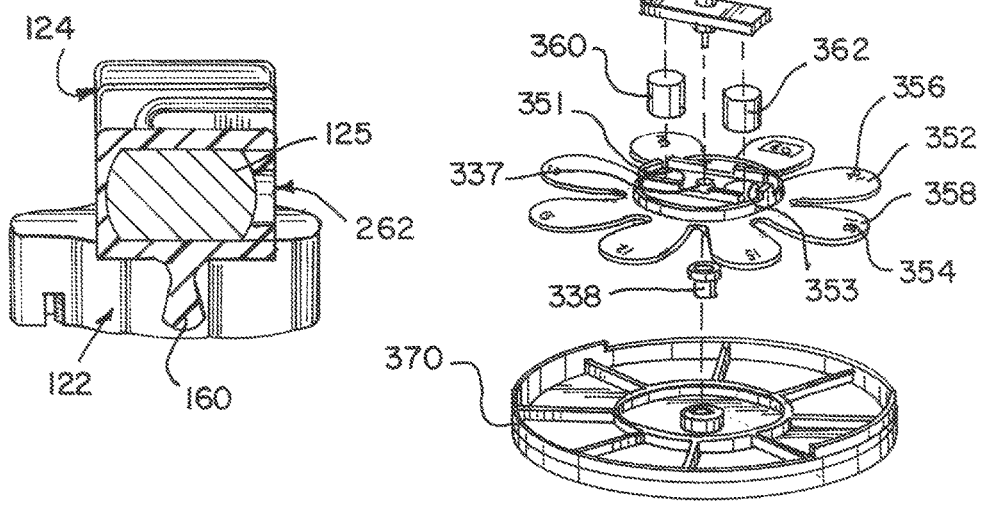

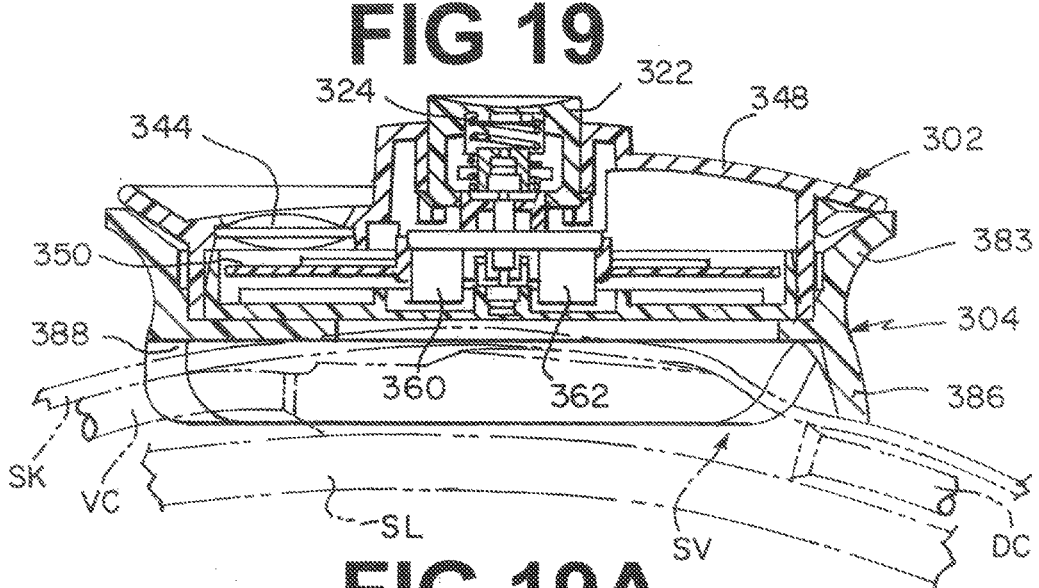
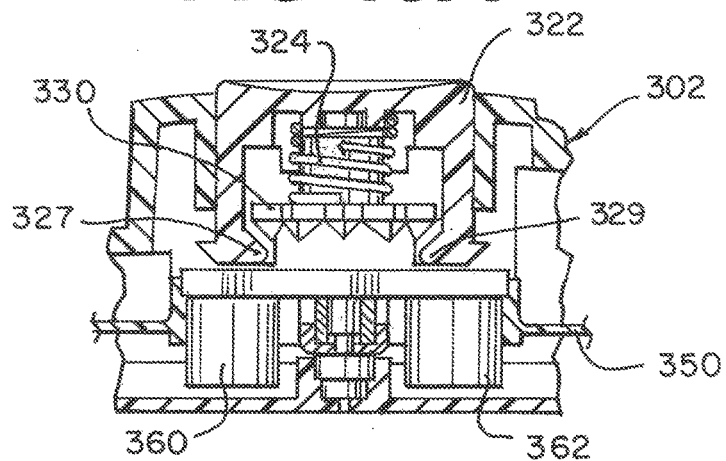
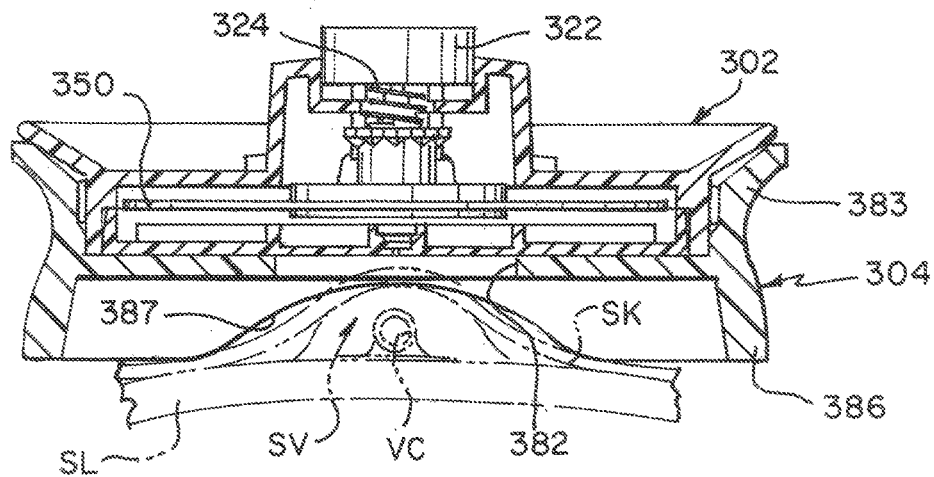

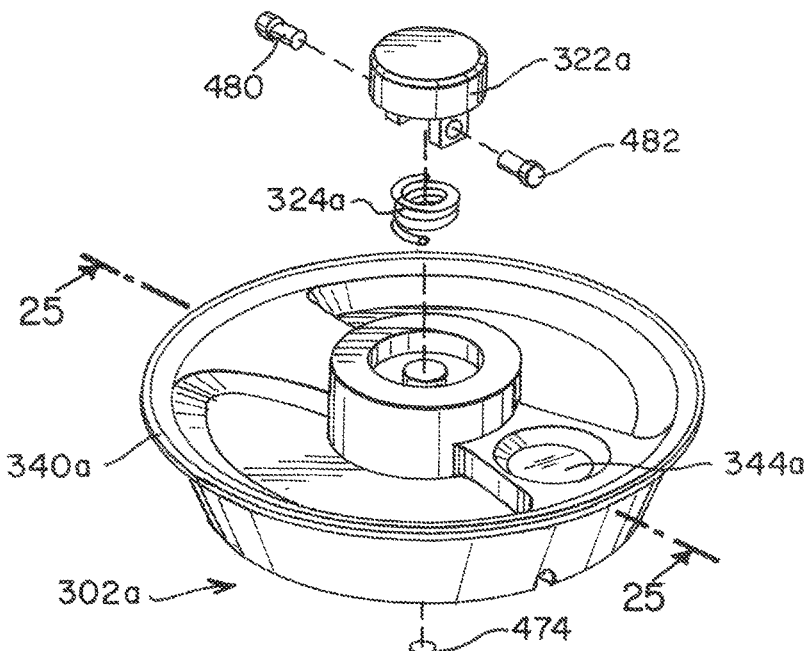
FIG 24
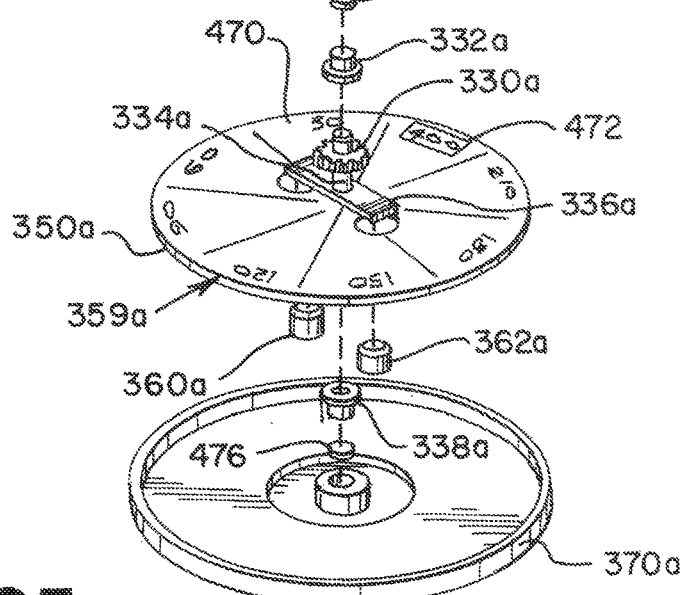
FIG 25
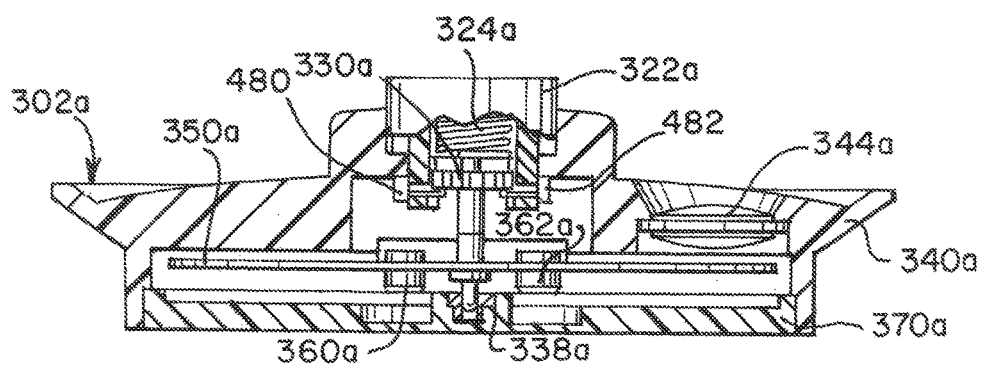

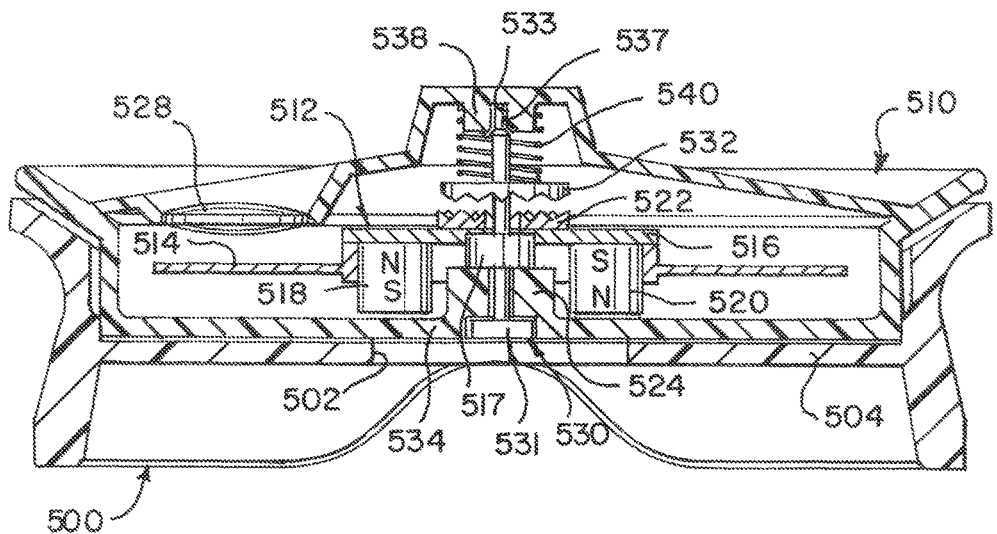
FIG 26
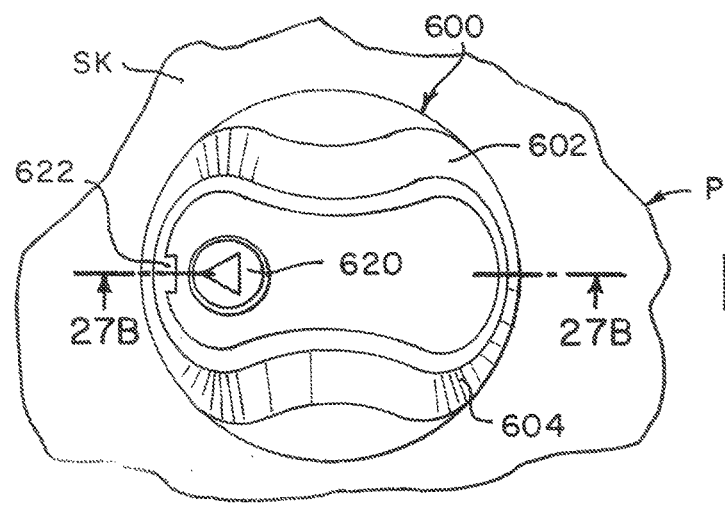
FIG 27A
FIG 30
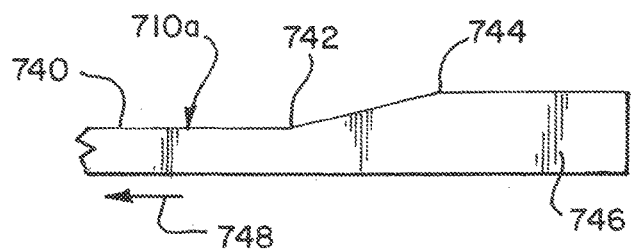

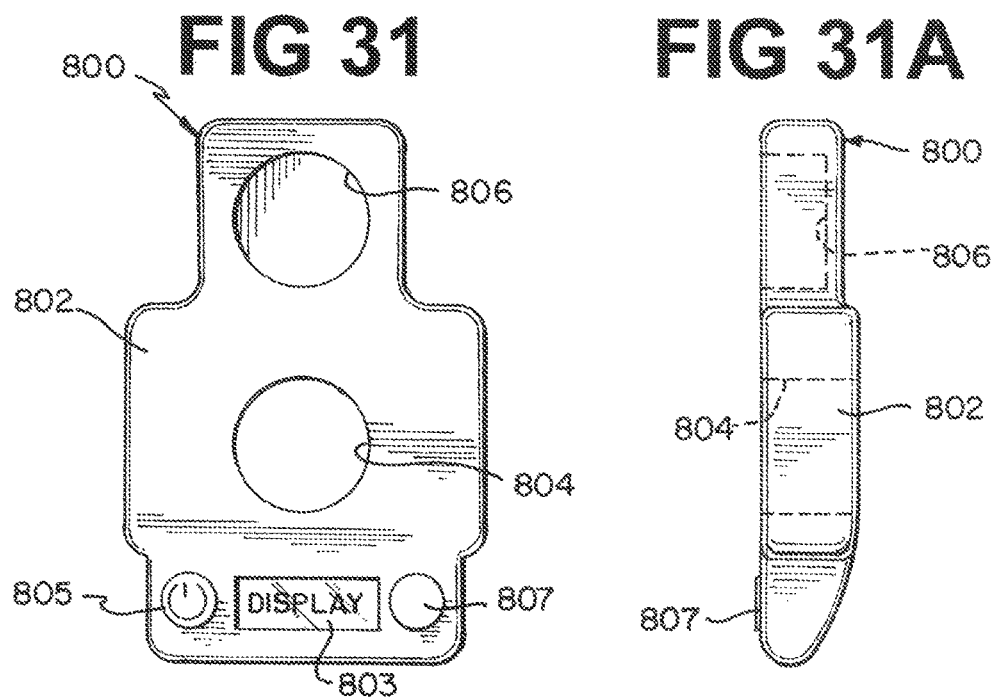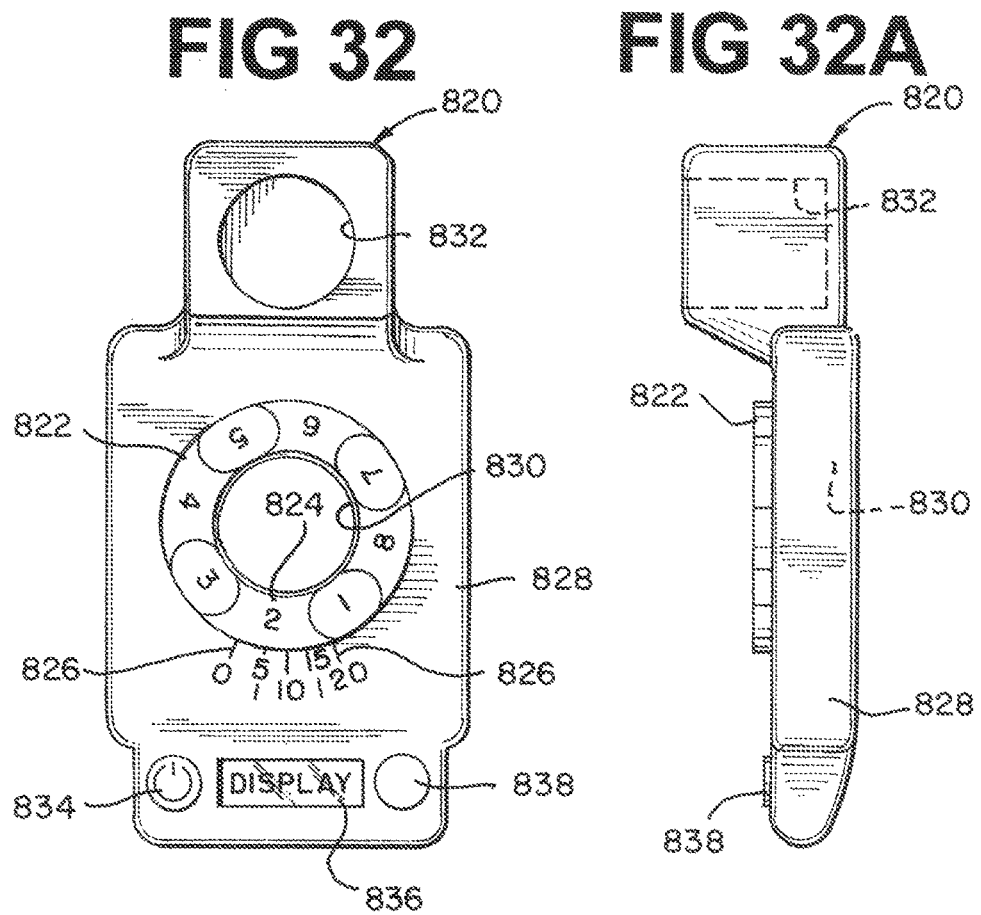

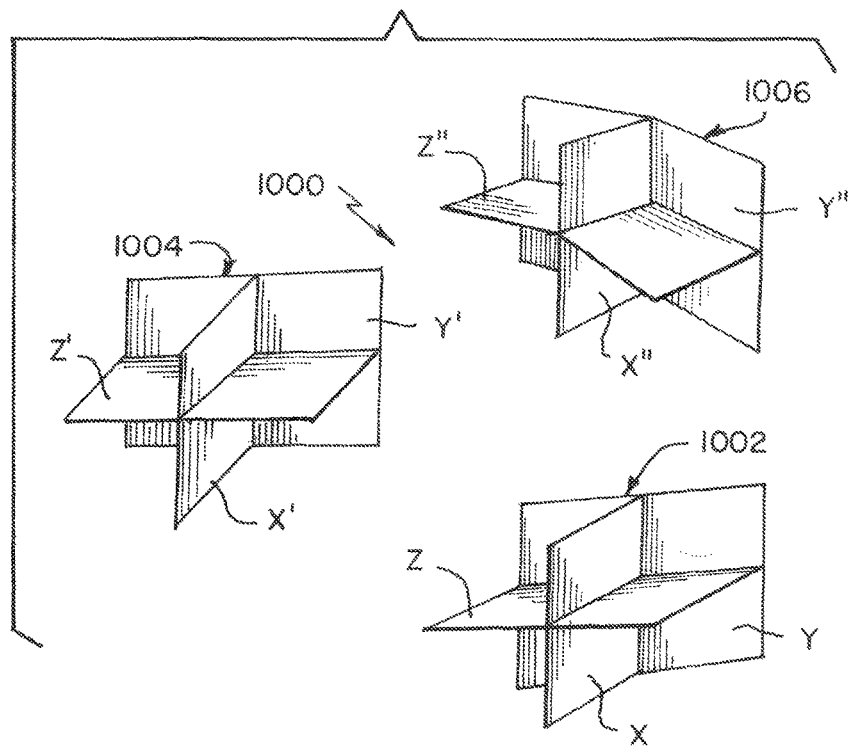
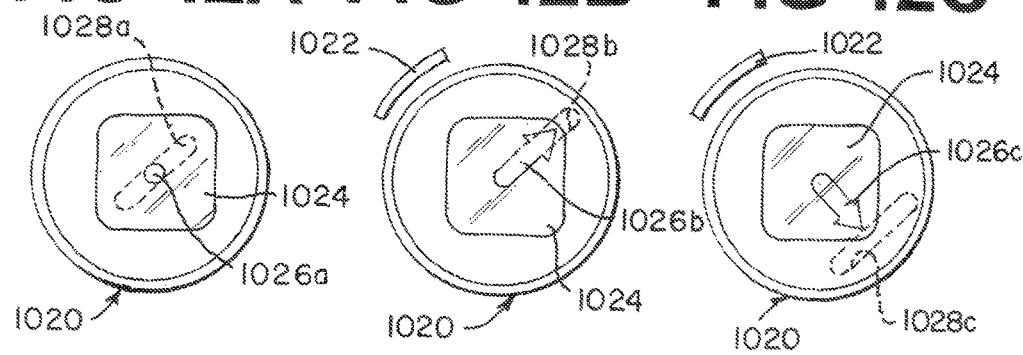

METHOD AND TOOLS FOR IMPLANTED DEVICE

CROSS-REFERENCE TO RELATED APPLICATIONS

This application is a divisional of U.S. application Ser. No. 14/725,240, filed on May 29, 2015 which is a divisional of U.S. application Ser. No. 13/929,998, filed on Jun. 28, 2013, which is a continuation-in-part of U.S. application Ser. No. 13/705,009, filed on Dec. 4, 2012, which is a divisional of U.S. application Ser. No. 12/858,193 filed Aug. 17, 2010, now U.S. Pat. No. 8,322,365, both of which are incorporated herein by reference in their entirety.

BACKGROUND OF THE INVENTION

1. Field of the Invention

The invention relates to techniques and tools to determine location, orientation and adjustment of implanted medical devices and more particularly to location, orientation and adjustment of adjustable valve mechanisms which resist unintentional performance setting changes.

2. Description of the Related Art

There are a number of treatments for medical conditions which require fluid to be removed from an organ or tissue of a patient. One such condition is hydrocephalus, where cerebrospinal fluid abnormally accumulates in the skull faster than it is withdrawn by the body. The excessive build-up of cerebrospinal fluid compresses brain tissues, which eventually leads to brain damage.

Hydrocephalus is commonly treated by implanting a shunt in fluid communication with a ventricle within the brain to withdraw cerebrospinal fluid at a desired rate. Typically, the rate of withdrawal of cerebrospinal fluid is controlled by a valve having different pressure settings which a clinician adjusts pre-operatively. A number of shunt valves can be noninvasively changed after implantation, such as the Codman® Hakim® programmable valve which is currently commercially available from Codman & Shurtleff, Inc. of Raynham, Mass. Other adjustable valves include the Strata™ valve from Medtronic Neurosurgery, the ProGAV™ valve manufactured by Christoph Meithke GMBH and distributed by Aesculap AG, and the Sophy™ and Polaris™ valves available from Sophysa USA Inc. All of these valves utilize applied magnet fields, such as those generated by magnets, to adjust valve pressure settings. To differing degrees, these valves are not optimal regarding resistance to unintentional setting changes, ease of use in achieving the desired valve setting, and detection of actual valve setting.

Detection of one or more parameters of an implanted device is disclosed generally by Hakim et al. in U.S. Pat. No. 4,608,992. Non-invasive adjustment of implanted valves is described generally by Hooven in U.S. Pat. No. 4,676,772. Some techniques for determining the location and orientation of an indwelling medical device are disclosed by Haynor et al. in U.S. Pat. Nos. 5,879,297 and 6,216,028. More recent techniques and tools include those disclosed by Bertrand et al. in U.S. Patent Publication Nos. 2002/0022793 and 2005/0092335, and by Girardin et al. in U.S. Patent Publication No. 2011/0105993, for example.

Magnetic resonance imaging, also referred to as MRI, is an increasingly common procedure for examining one or more regions of a patient. MRI provides better contrast between tissue types than computed tomography and utilizes powerful magnetic fields instead of potentially harmful x-rays. While magnetic exposure levels from first generation MRI systems were typically up to 1.5 Tesla, newer MRI machines routinely use 3.0 Tesla. As recognized by McCusker et al. in U.S. Pat. No. 7,390,310, for example, such strong magnetic fields can interfere with implanted devices including shunt valves.

As of the filing date for the present application, the Codman® CERTAS™ programmable valve is currently commercially available from Codman & Shurtleff, Inc. of Raynham, Mass. The CERTAS™ valve was disclosed and claimed in the parent application, now U.S. Pat. No. 8,322,365, and is generally resistant to MRI exposure up to at least 3.0 Tesla without unintentionally changing the valve setting. Intentional valve adjustment is accomplished using a suitably aligned magnetic field. Correct positioning of the applied magnetic field relies on the user.

It is therefore desirable to have simplified and more accurate techniques and tools to locate, determine orientation, and adjust implantable valves capable of withstanding strong magnetic fields and which resist unintended changes to valve settings.

SUMMARY OF THE INVENTION

An object of the present invention is to provide an improved method and tools to locate, determine orientation, and adjust as desired an implanted valve unit which resists unintentional performance setting changes when the unit is subjected to vibration, jarring or unintended magnetic fields.

Another object of the present invention is to provide such positioning methods and tools which readily and accurately allow desired non-invasive changes to pressure or flow control settings of the implanted valve unit.

It is yet another object of this invention to enhance detection of the actual valve opening pressure setting or flow control setting.

This invention features a method of positioning a toolset on the exterior of a patient relative to a magnetically adjustable device implanted in the patient, the implanted device including a rotor having an axis of rotation and at least one rotor magnet, the rotor having a range of arcuate motion within each of a plurality of selectable performance settings without altering a selected performance setting for the implanted device. The method includes estimating a location on the exterior of the patient above the implanted device, moving the toolset to the estimated location, detecting the location of at least one of a maximum positive pole value and a maximum negative pole value of the rotor magnet at a current performance setting, and moving the toolset relative to the at least one detected maximum pole value. Preferably, the method further includes moving the rotor in a first arcuate direction and detecting a first limit of travel without altering the current performance setting, moving the rotor in a second, opposite direction and detecting a second limit of travel without altering the current performance setting, comparing the first and second limits of travel with known values for the plurality of selectable performance settings, and indicating the current performance setting of the implanted device.

In some embodiments, the implanted device is a valve unit having adjustable performance settings to regulate passage of a bodily fluid. The valve unit includes a casing defining a port, such as an inlet or an outlet for the bodily fluid, and a valve mechanism positioned at the port. The valve mechanism includes a movable valve member. The valve unit further includes a rotor disposed at a first location in the casing and having an axle which turns about an axis of rotation. The rotor defines a plurality of radially flat cam surfaces, each cam surface occupying an arc about the axis of rotation. A spring arm unit, disposed at a second location in the casing, has a cam follower arm in slidable contact with the cam surfaces of the rotor and has a resilient spring element applying a closing effect with the valve member at the port to establish a performance setting for the valve unit. Sufficient rotation of the rotor to change the cam surface in contact with the cam follower alters the closing effect with which the valve member moves relative to the port and thereby alters the performance setting of the valve unit.

This invention also features a positioning toolset suitable for indicating and adjusting the current performance setting of a magnetically adjustable device implanted in a patient, the implanted device having at least one magnet aligned with the current performance setting of the device. The toolset includes an indicator tool with at least one sensor that detects the location of the implanted device and determines the current performance setting of the implanted device. The indicator tool is capable of guiding a user to move the indicator tool to an optimum position relative to the implanted device and including at least one locating feature to designate the optimum position of the indicator tool. The toolset further includes an adjustment tool having at least one adjustor magnet and at least one locating feature to align the adjustment tool with the optimum position of the indicator tool, the adjustor magnet being movable relative to the at least one locating feature to change the performance setting of the implanted device.

In some embodiments, the at least one locating feature of the indicator tool is independent from the at least one locating feature of the adjustment tool. In one embodiment, at least one of the locating features of the indicator tool and the adjustment tool is a marking guide capable of assisting a user in placing and aligning a reference mark on a patient.

BRIEF DESCRIPTION OF THE DRAWINGS

In what follows, preferred embodiments of the invention are explained in more detail with reference to the drawings, in which:

FIG. 1A is a side cross-sectional view of an alternative programmable shunt valve device having another novel adjustable valve unit;

FIG. 3 is a top view of the adjustable valve unit of FIG. 2;

FIG. 4 is a side cross-sectional view of the adjustable valve unit of FIG. 3 along lines 4-4;

FIGS. 6B-6H are partial cross-sectional views of the adjustable valve unit of FIG. 4 at different, successive pressure settings;

FIG. 10 is a side cross-sectional view of the adjustable valve unit of FIG. 8 along lines 10-10 showing axial lifting of the rotatable construct;

FIG. 11 is a shallower partial top cross-sectional view of the adjustable valve unit of FIG. 6H showing the "virtual off" position in an unconstrained condition;

FIG. 12 is a side view along lines 12-12 of FIG. 11;

FIG. 13 is a side cross-sectional view along lines 13-13 of FIG. 11;

FIG. 13A is a partial cross-sectional view along lines 13A-13A of FIG. 13;

FIG. 14 is a perspective view of a tool set according to the present invention including an indicator tool, a locator tool, and a setting adjuster tool;

FIG. 15 is an exploded perspective view of the indicator tool of FIG. 14;

FIG. 19 is a side cross-sectional view along lines 19-19 of FIG. 18 with a release button in a normal, engaged position;

FIG. 19A is a partial side cross-sectional view along lines 19-19 of FIG. 18 showing the release button in a depressed, disengaged position;

FIG. 20 is a partial cross-sectional view along lines 20-20 of FIG. 18;

FIG. 24 is an exploded view of an alternative indicator tool according to the present invention;

FIG. 25 is a side cross-sectional view along lines 25-25 of FIG. 24;

FIG. 26 is a cross-sectional view of another alternative indicator tool according to the present invention positioned in a locator tool;

FIG. 27A is a top plan view of an adjuster tool positioned over a patient with the locator tool omitted;

FIG. 30 is a schematic side view of yet another movable valve member;

FIGS. 31 and 31A are schematic top and side views of a positioning tool of a positioning toolset according to the present invention;

FIGS. 32 and 32A are schematic top and side views of an alternative positioning tool according to the present invention;

FIG. 40 is a schematic diagram of three sensor arrays for a positioning tool according to the present invention, each array sensing X, Y and Z axes;

FIGS. 42A-42C are top views of alternative displays guiding a user;

DETAILED DESCRIPTION OF THE PRESENTLY PREFERRED EMBODIMENTS

Several constructions of a positioning toolset, also referred to as a positioning system, according to the present invention have a positioning tool and an adjustment tool such as shown and described below in relation to FIGS. 14-47. This invention may be accomplished by positioning a toolset on the exterior of a patient relative to a magnetically adjustable device, such as a valve unit implanted in the patient. The implanted valve unit or other device includes a rotor having an axis of rotation and at least one rotor magnet, the rotor having a range of arcuate motion within each of a plurality of selectable performance settings without altering a selected performance setting for the implanted device. The method includes estimating a location on the exterior of the patient above the implanted device, moving the toolset to the estimated location, detecting the location of at least one of a maximum positive pole value and a maximum negative pole value of the rotor magnet at a current performance setting, and moving the toolset relative to the at least one detected maximum pole value. Preferably, the method further includes moving the rotor in a first arcuate direction and detecting a first limit of travel without altering the current performance setting, moving the rotor in a second, opposite direction and detecting a second limit of travel without altering the current performance setting, comparing the first and second limits of travel with known values for the plurality of selectable performance settings, and indicating the current performance setting of the implanted device. Certain details on the method are provided below in relation to FIGS. 35-39.

A preferred application for an adjustable valve unit suitable for use according to the present invention is within a single use implantable valve device as part of a system for shunting cerebrospinal fluid to treat hydrocephalus. It is desirable for the valve unit to have a number of different pressure settings for constant, controlled intraventricular pressure and drainage of cerebrospinal fluid. Preferred opening pressure settings preferably range from approximately 30 mm to 210 mm water (294 Pa to 2,059 Pa) in seven increments of 30 mm (294 Pa), with a final setting of approximately at least 400 mm water (3,920 Pa) to minimize flow as a "virtual off" setting, that is, as substantially closed. A clinician can select and set the initial opening pressure of the valve pre-operatively. After implantation, the pressure setting can be changed noninvasively using a toolset according to the present invention.

Figure 1:
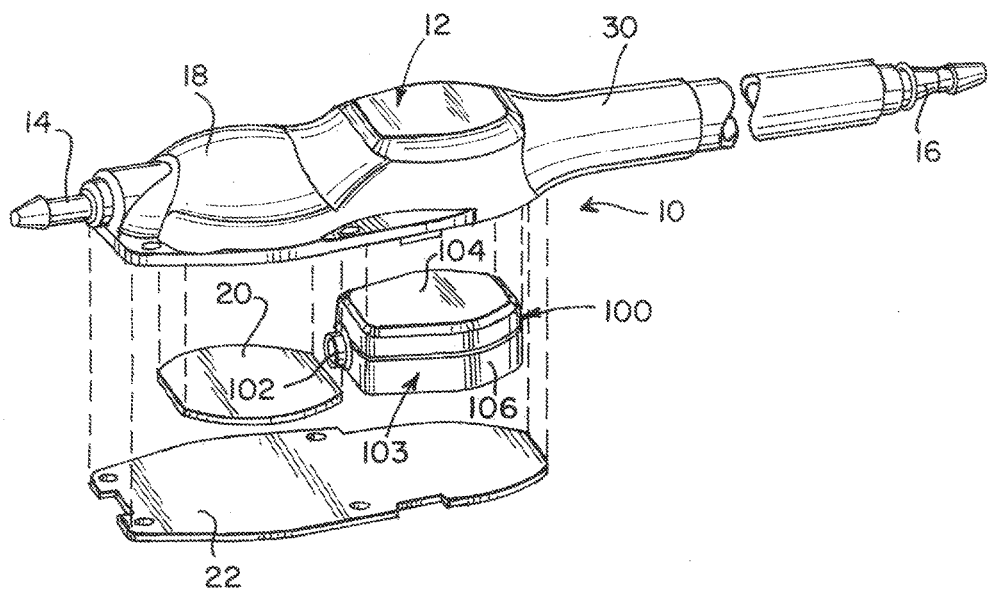
FIG. 1 is a schematic perspective exploded view of a novel programmable shunt valve device having an improved adjustable valve unit.

FIG. 1 illustrates a programmable shunt valve device 10 having a shunt housing 12, preferably formed of a translucent material such as silicone, with proximal connector 14 and distal connector 16. A ventricular catheter or other proximal catheter is connectable to connector 14 to bring fluid into shunt housing 12. Fluid passes into sampling or pumping chamber 18 and then through a valve mechanism in inlet 102 into novel adjustable valve unit 100, which is shown and described in more detail below in relation to FIGS. 2-13A. Valve unit 100, FIG. 1, includes a casing 103 formed as upper casing 104 and lower casing 106 which are joined by sonic welding in this construction. A needle guard 20, preferably formed of a rigid polymeric material, and lower casing 106 are secured within housing 12 by a backing plate 22, preferably formed of silicone reinforced with a polymeric mesh, which is bonded to housing 12 by a medical grade epoxy.

When fluid pressure at inlet 102 exceeds a selected pressure setting within valve unit 100, fluid is admitted past a valve mechanism and then flows through valve unit outlet 110 into passage 30 of housing 12. Preferably, a Siphonguard® device, which is currently commercially available from Codman & Shurtleff, Inc. of Raynham, Mass., is disposed within passage 30. The Siphonguard® device (not shown) is designed to prevent excessive drainage of cerebrospinal fluid by a shunt system. One cause of excessive draining is a change in patient position from a supine to an upright position. Ultimately, fluid exits from housing 12 through distal connector 16 into a peritoneal catheter or other distal catheter.

An alternative shunt valve device 10a is shown in cross-section in FIG. 1A having a shunt housing 12a, proximal connector 14a with epoxy seals 13 and 15, and distal connector 16a with epoxy seals 17 and 19. Needle guard 20a and backing plate 22a form the floor of chamber 18a. Fluid flows into novel valve unit 100a through inlet 102a defined by lower casing 106a and exits through outlet 110a, defined by upper casing 104a in this construction, into a small chamber 40 and then directly into distal connector 16a. More details on the components within valve units 110 and 110a are provided below.

Figure 2:
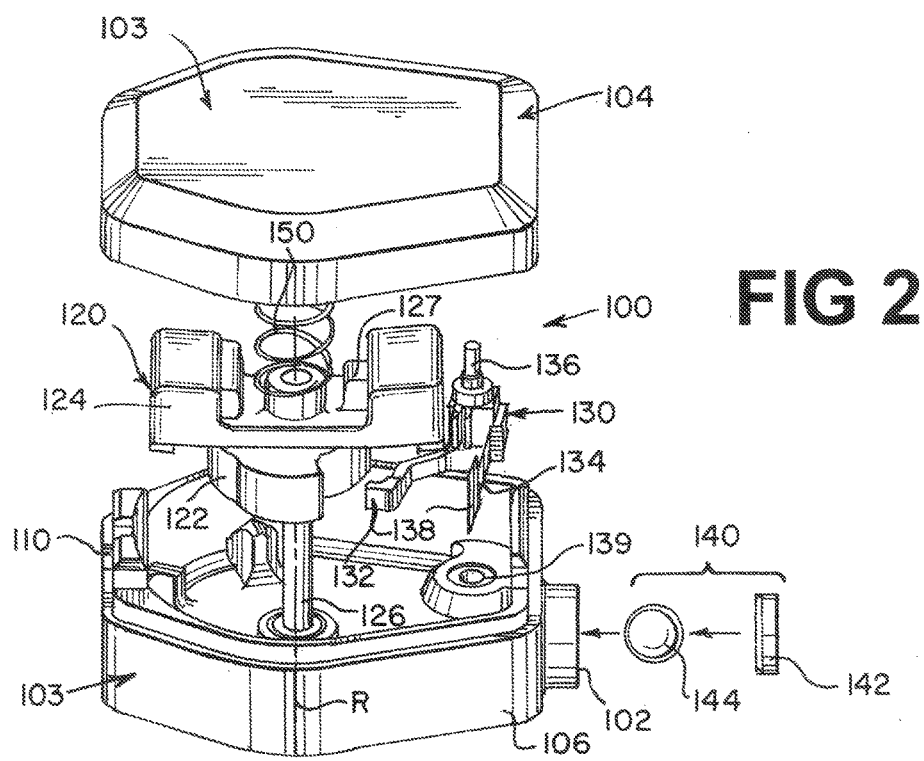
FIG. 2 is an exploded perspective view of the adjustable valve unit of FIG. 1.

Valve unit 100, FIG. 2, includes rotor 120, spring arm unit 130, valve mechanism 140, and a rotor retention spring 150. In this construction rotor 120, also referred to as a rotating construct, is formed of a lower cam structure 122 having a plurality of radially flat cam surfaces, as shown and described in more detail below, and an upper, magnet housing 124 carrying magnetic elements 123 and 125. Housing 124 also defines a finger 127 which engages a stop in upper casing 104 when rotor 120 is moved to an unconstrained condition as described below. Rotor 120 rotates about axle 126 which defines a substantially fixed axis of rotation R at a first location in casing 103.

Preferably, rotor 120 is also capable of moving along the axis of rotation, in a translational motion, to an unconstrained condition when an adjuster tool is applied to it as described in more detail below. Retention spring 150 biases rotor 120 to a downward, normally constrained condition. Preferably, spring 150 is a coil spring having sufficient bias to resist the effect of gravity, regardless of the position of the valve unit, and to resist magnetic or ferrous objects, such as magnets in an indicator tool described in more detail below. However, spring 150 is insufficient to resist the effects of an adjustment tool, also described below. Lower cam section 122 has a sufficient height to ensure that cam follower 132 remains in contact with a cam surface in both the constrained and unconstrained conditions.

Spring arm unit 130 includes cam follower 132, a resilient spring element 134, and upper and lower axles 136 and 138 at a second location in casing 103. Axle 138 turns about a bearing 139 formed of a low-friction, hard material such as synthetic ruby. It is desirable for casing 103, rotor 120 and spring arm unit 130 to be formed of polyethersulfone, while all spring components are formed of medical grade non-ferromagnetic stainless steel.

Valve mechanism 140 includes seat 142 and movable valve member 144. Preferably, seat 142 and valve member 144, such as a ball, are formed of the same non-ferromagnetic material such as synthetic ruby. In other constructions, the movable valve member may be a disc, a cone, or other type of plug. A spherical ball is currently preferred because that shape enables tight, precise tolerances, assembly and control relative to the valve seat. Also, the position of the seat within a port can be adjusted during assembly of the valve unit to alter the actual performance value achieved at each setting, using a force versus displacement relationship. First, a mandrel checks the position of the ball, and the seat is inserted at an estimated desirable location within the port. Ball displacement is tested at one or more settings to confirm that desired performance will be achieved.

Valve unit 100a, FIG. 1A, includes a monolithic rotor 120a having pockets carrying magnetic elements 125a and 123a each having north N and south S magnetic orientations. Instead of a separate housing element which is molded independently and then attached to the lower rotor unit to form a combined rotor construct such as shown in FIGS. 1 and 2, rotor 120a is a different type of rotating construct that is micro-molded with pockets in the upper housing portion 124a of the rotor 120a together with lower cam portion 122a. Magnetic elements 123a, 125a and tantalum reference ball 129a then are placed in the pockets. Thereafter, epoxy such as Loctite® M-31CL™ epoxy is added to fill in remaining voids in the pockets to complete the rotor 120a. Axle 126a is shown as a separate component which is added to rotor 120a after it is removed from the micro-mold; in another construction, axle 126a is co-molded with the main rotor 120a. Also shown in FIG. 1A are rotor teeth 160a and 162a, movable valve element limiter 180a and a portion of spring element 134a pressing ball 144a against valve seat 142a. In an alternative construction, rotor teeth 160a, 162a are positioned below the cam portion 122a instead of projecting below the housing portion 124a as illustrated.

Figure 5:
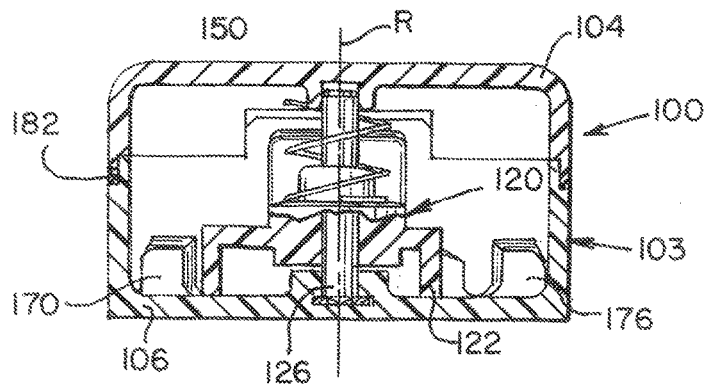
FIG. 5 is a cross-sectional view of the adjustable valve unit of FIG. 3 along lines 5-5.

Valve unit 100 is shown assembled in FIGS. 3-5 and positioned at a second pressure setting, as described in more detail below. Rotor housing 124 carries downwardly projecting teeth 160 and 162 with cooperate with four lock stops projecting upwardly from lower casing 106 in this construction. Lock stop 172 is shown in partial cross-section in FIG. 4 and lock stops 170 and 176 are visible in FIG. 5. Preferably, the lower surfaces of rotor teeth 160 and 162 are rounded and the upper surfaces of casing lock stops 170, 172, 174 and 176 each have a plurality of facets to create a chisel-like, lead-in topography which encourages the rotor teeth to return to a constrained position. However, the vertical surfaces of teeth 160, 162 and of stops 170-176 abut when engaged and do not "lead out", that is, relative translational movement is discouraged. Pure vertical lift must be provided by an adjustment tool, as described in more detail below, to overcome the tooth-to-stop abutment and change the performance setting.

A limiter 180, FIG. 4, restricts travel of spring 134 away from seat 142 so that ball 144 does not become misaligned or dislodged relative to seat 142. A gasket 182 of epoxy is shown in FIGS. 4 and 5 as an optional, redundant seal between upper casing 104 and lower casing 106 in this construction.

Figure 6:
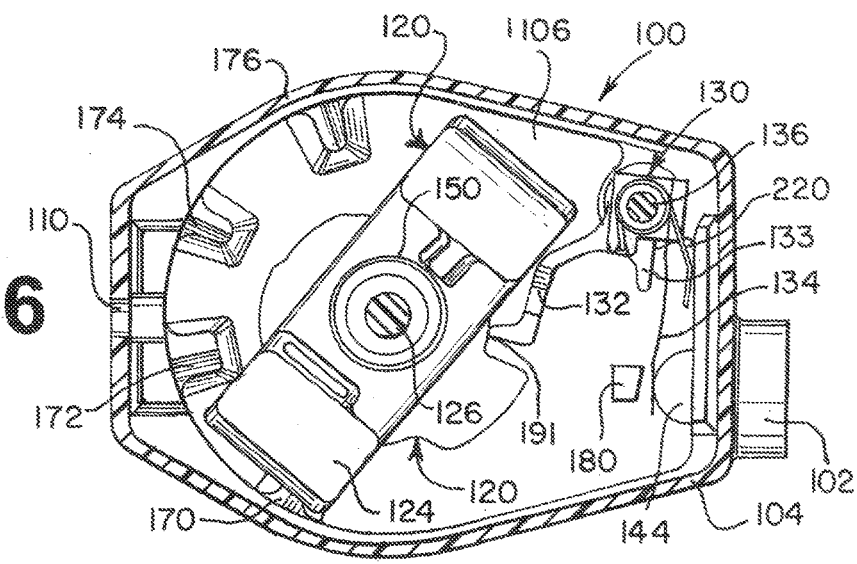
FIG. 6 is a partial cross-sectional view of the adjustable valve unit of FIG. 4 approximately along lines 6-6 at a first pressure setting.
Figure 6A:
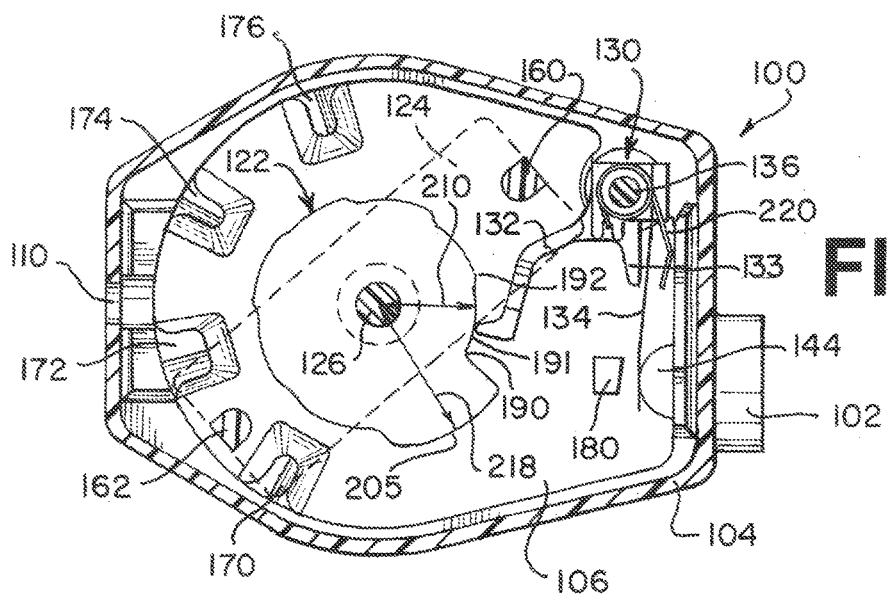
FIG. 6A is a deeper cross-sectional view of the adjustable valve unit of FIG. 4 approximately along lines 6A-6A at a first pressure setting.
Figure 7:
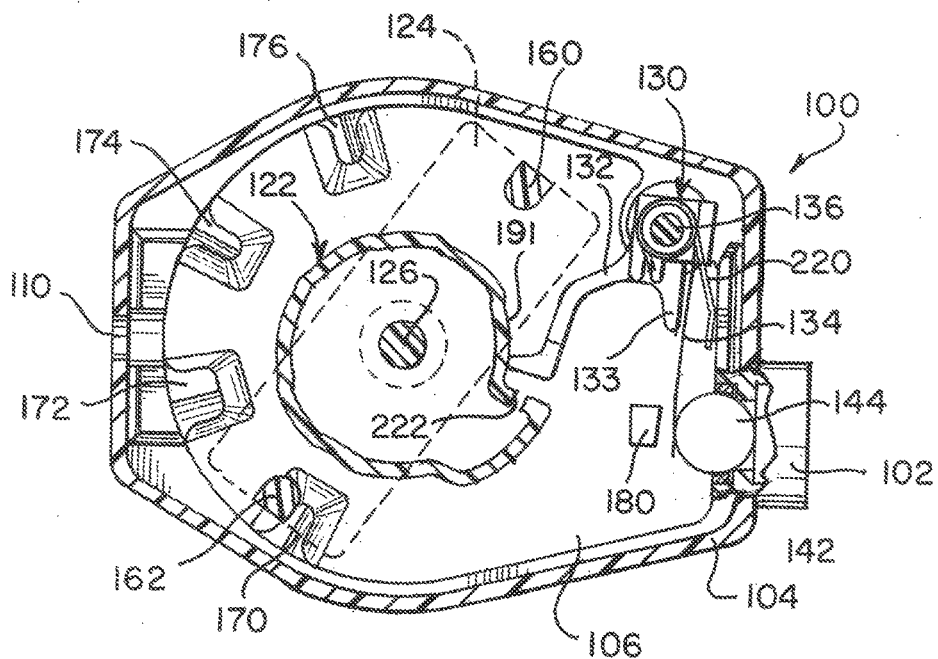
FIG. 7 is a deeper cross-sectional view of the adjustable valve unit of FIG. 4 approximately along lines 7-7.
Figure 8:
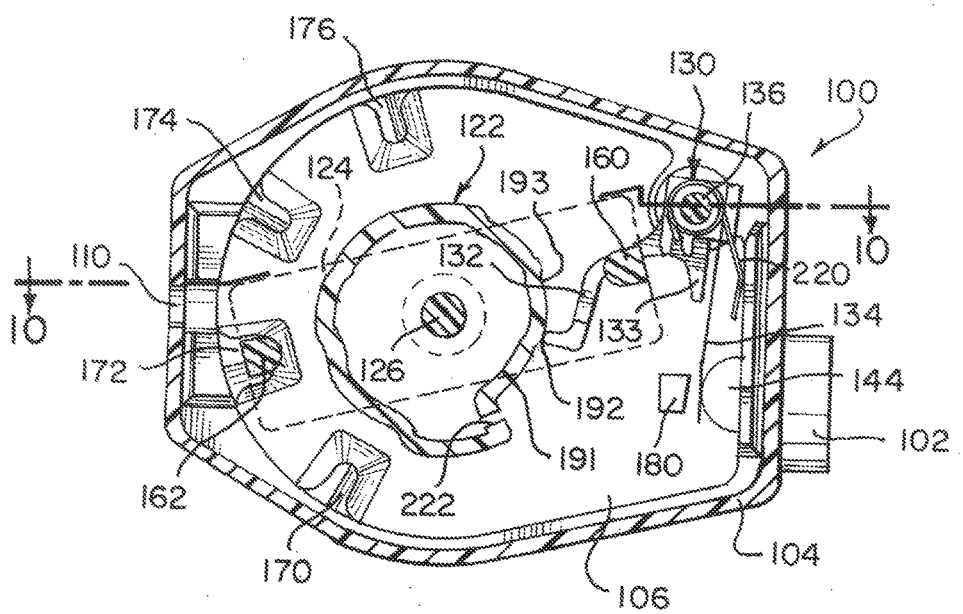
FIG. 8 is a cross-sectional view of the adjustable valve unit of FIG. 7 showing the transition to a different pressure setting.

The operation of valve units 100 and 100a are similar and are illustrated in FIGS. 6-8 in relation to valve unit 100, with identical reference numerals identifying identical components and features. Not all such components and features are labelled in each drawing for the sake of visual clarity. FIGS. 6 and 6A show different levels of top partial cross-sectional views for valve unit 100 at a first pressure setting. Cam follower 132 slidably contacts only a first cam surface 191, which has an arc length bounded by points 190 and 192, because rotor housing tooth 162 is captured between casing lock stops 170 and 172 in the normal, constrained condition. First cam surface 191 has a first, preferably shortest radial distance 210 relative to the axis of rotation of rotor 120. By comparison, outermost cam surface 205 has a greatest radial distance 218 as described in more detail below. An optional torsion spring 220 is shown in greater detail in FIG. 9.

When rotor 120 is translated upwardly by magnets in an adjustment tool as described below, rotor tooth 162 is lifted so that subsequent clockwise or counter-clockwise rotation of the adjustment tool rotates tooth 162 up and over casing lock stop 172. After the adjustment tool is removed and when the second pressure setting has been selected as shown in FIG. 6B, rotor 120 is biased downwardly by spring 150, FIGS. 2, 4 and 5.

Figure 6B:
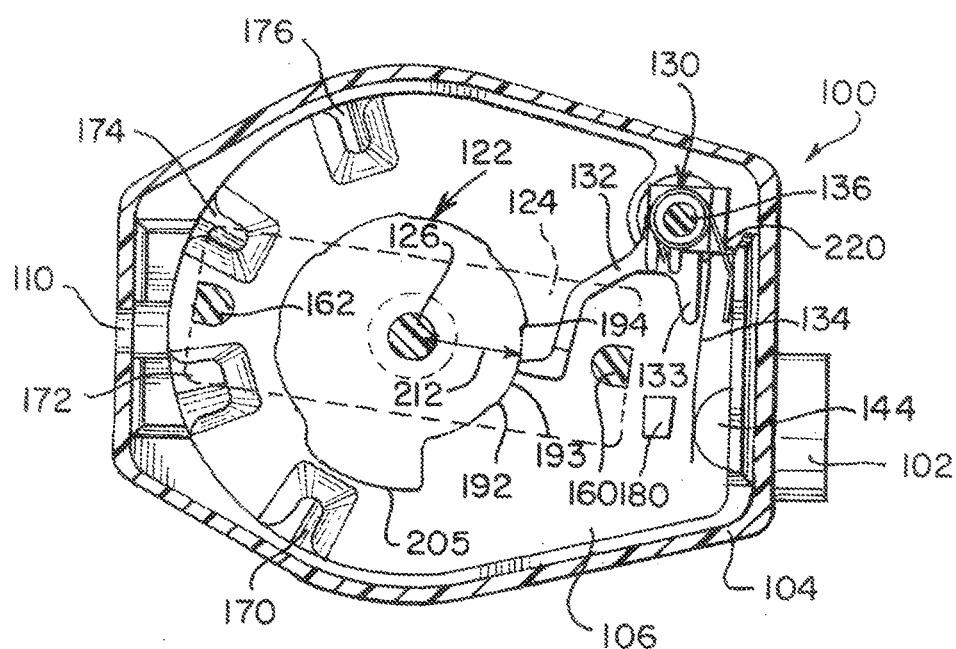

Rotor tooth 160 is illustrated as not being in contact with any stop in FIGS. 4 and 6B, for example, because in the constrained condition rotor tooth 162 is now captured between a pair of lock stops 172 and 174, FIG. 6B, which is sufficient to prevent rotation of rotor 120 relative to the cam follower 132 beyond points 192 and 194 on the cam structure of rotor 120. Points 192 and 194 represent a second arc length for second cam surface 193. Surface 193 is at a second radial distance 212 which is greater than distance 210 and is less than distance 218, FIGS. 6A and 6H. The arc length of second cam surface 193, FIG. 6B, can be the same or different than the arc length of first cam surface 191 but, preferably, is substantially the same length.

The outward radial motion of cam follower 132 as it slidably travels from first cam surface 191, FIG. 6A, to second cam surface 193, FIG. 6B, increases the biasing force by valve spring 134 on ball 144 as increased torque is applied by cam follower 132 to the remainder of spring arm unit 130. Improved precision in pressure control is achieved by having a stiff cam follower 132 in contact with the selected cam surface and a flexible element, spring 134, in contact with the valve ball 144. The enhanced result is opening of the ball 144 from the valve seat 142 by requiring only the resilient spring element 134 to bend, which provides a constant spring force to the ball 144. The opening pressure, and overall valve performance, is not reliant on axial pivoting of the spring arm unit 130.

Figure 6C:
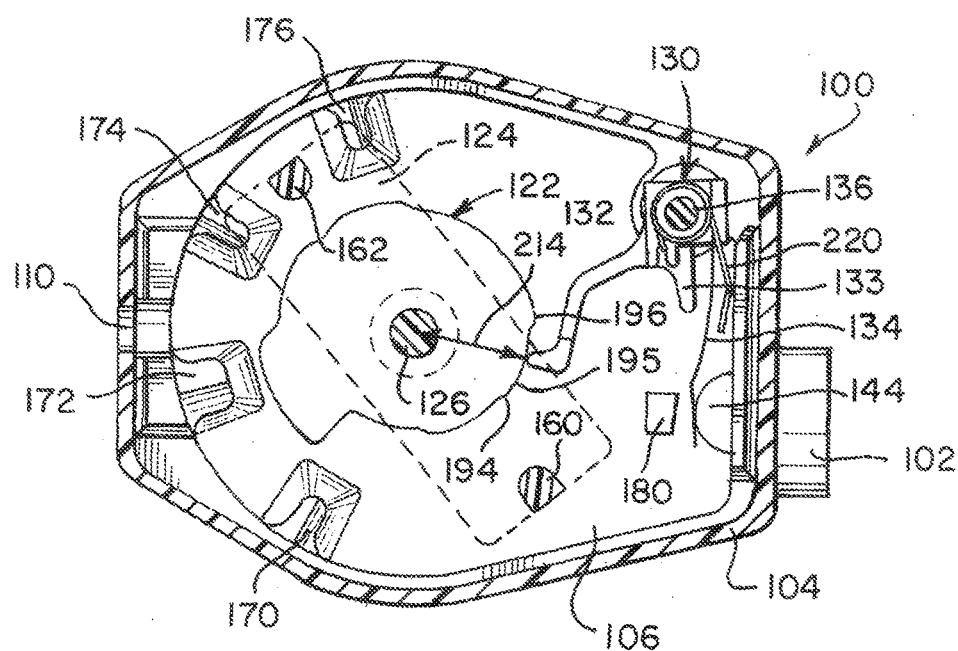

A third opening pressure setting is shown in FIG. 6C with rotor tooth 162 positioned between casing stops 174 and 176 such that cam follower 132 experiences only third cam surface 195 between points 194 and 196 at a third radial distance 214. To achieve a fourth pressure setting, FIG. 6D, both rotor teeth 160 and 162 are utilized relative to casing stops 170 and 176, respectively. Cam follower 132 is restricted thereby to fourth cam surface 197 between points 196 and 198.

Figure 6F:
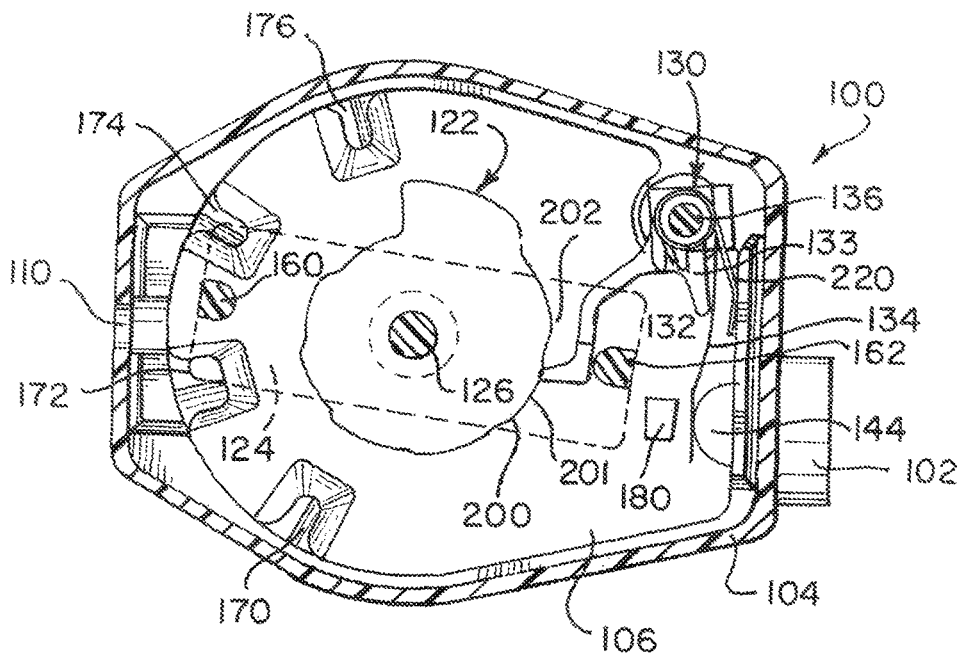
Figure 6G:
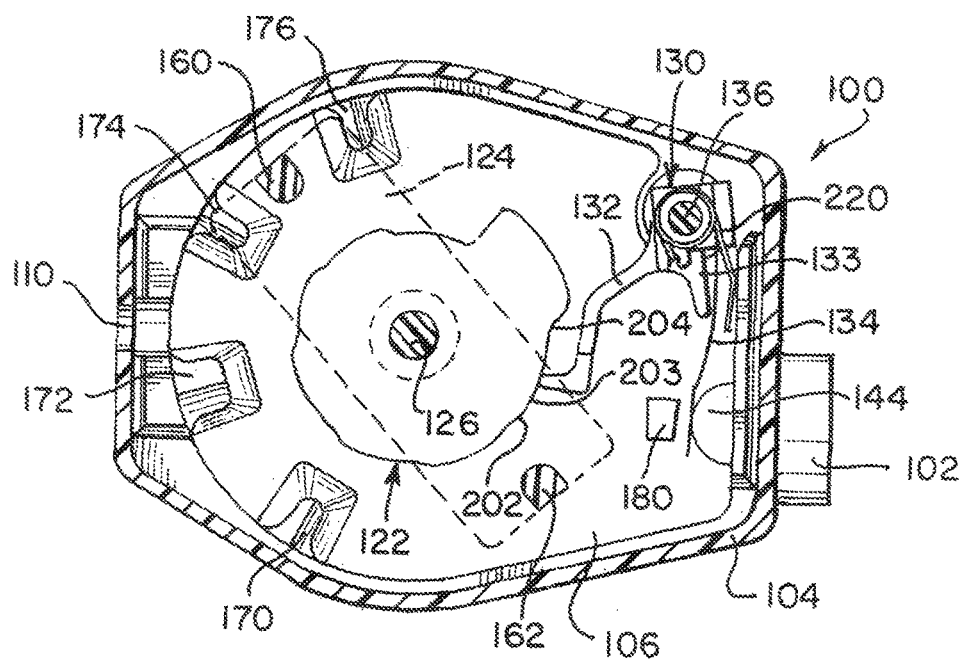

Fifth through seventh pressure settings are illustrated in FIGS. 6E-6G as rotor tooth 160 is successively captured between casing lock stop pairs 170-172, 172-174, and 174-176, respectively. Cam follower 132 is restricted thereby to fifth cam surface 199 between points 198 and 200, FIG. 6E, sixth cam surface 201 between points 200 and 202, FIG. 6F, and seventh cam surface 203 between points 202 and 204, FIG. 6G.

Preferred opening pressure settings currently range from approximately 30 mm to 210 mm water (294 Pa to 2,059 Pa) in seven increments of 30 mm (294 Pa), with a final, "virtual off" setting described in more detail below. Preferably, each valve unit is calibrated and tested at the time of manufacture at one or more flow rates. Actual opening pressure for each setting tends to vary according to flow rate, typically measured in milliliters per hour. Also, when tested with a 120 cm long distal catheter having an inner diameter of 1 mm, the average opening pressure typically will increase by 9 mm water or more at flow rates of 5 ml/h or more.

Figure 6H:
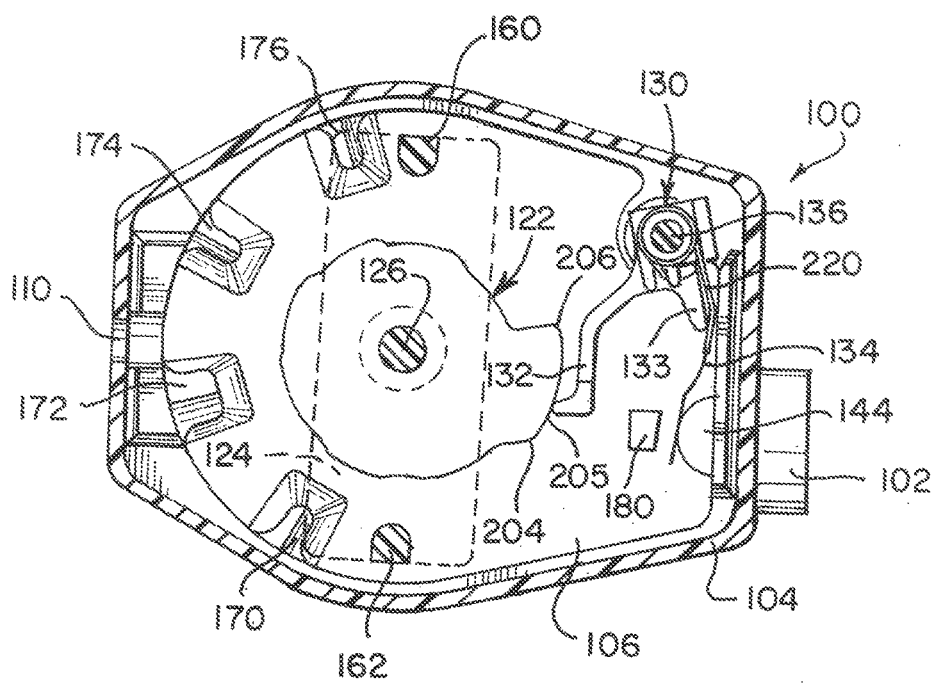

The final setting, FIG. 6H, of approximately at least 400 mm water (3,920 Pa) minimizes flow as a "virtual off" setting, that is, as substantially closed. This final setting is achieved by exposing cam follower 132 to outermost cam surface 205, defined by points 204 and 206, having greatest radial distance 218. This greatest cam setting forces stiffener element 133 of spring arm unit 130 against valve spring 134 to shorten its active, effective length and thereby dramatically increase the biasing force applied against ball 144. The final opening pressure is increased by more than fifty percent over the prior setting. In other constructions, a stiffener element is forced against a valve spring during two or more final cam settings at desired pressure increments.

Figure 9:
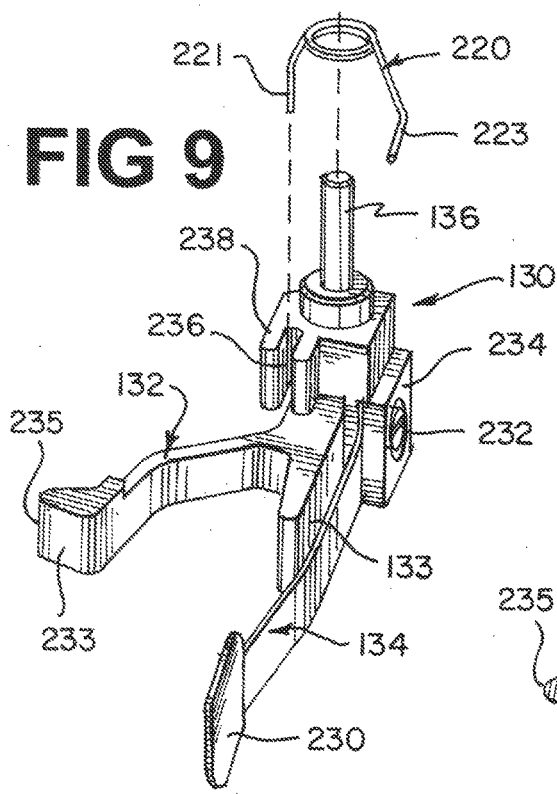
FIG. 9 is a perspective view of the spring arm unit with optional torsion spring.
Figure 9A:
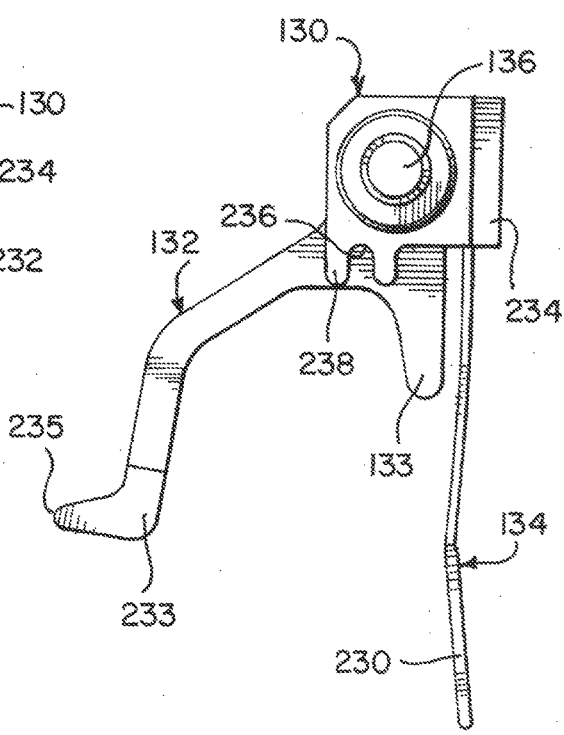
FIG. 9A is a top plan view of the element of FIG. 9.

Spring arm unit 130 is shown in greater detail in FIGS. 9 and 9A with cam follower 132, stiffener element 133, and valve spring 134. Cam follower 132 terminates in a triangular head 233 with rounded or chamfered edges, one of which serves as a bearing surface 235. In a preferred construction, spring element 134 is formed from stainless steel having a thickness of 0.020 inches and terminates in an enlarged pad 230 for contacting the valve ball or other movable valve member. In one construction, spring element 134 is attached to the remainder of spring arm unit 130 by a post 232 and rivet 234 which are secured by ultrasonic welding. Torsion spring 220 has a first leg 221 which is retained in recess 236 of projection 238. Second spring leg 223 rests against an inner surface of the casing.

Use of torsion spring 220 is optional, and is possible because only spring element 134 contacts the movable valve member. As a result, additional spring force from torsion spring 220 can be utilized to force bearing surface 235 of cam follower 132 against a cam surface of the rotor. This biasing force provided by torsion spring 220 augments rotational position of the spring arm reflective of the intended cam displacement without otherwise impacting the force applied to the ball or other movable valve member. This provides for a more accurate and repeatable opening pressure and a more manufacturable and robust design as it reduces the need to maintain minimal friction such as when the valve spring element solely provides the force needed to maintain the cam follower on the cam surface.

The position of the components and features within valve unit 100 at the first pressure setting shown in FIG. 6A is illustrated at a deeper partial cross-sectional view in FIG. 7. Opening 222 into the lower cam portion of rotor 120 inhibits negative pressure from developing under rotor 120, that is, opening 222 ensures pressure equalization as cerebrospinal fluid passes through valve unit 100.

Figure 23:
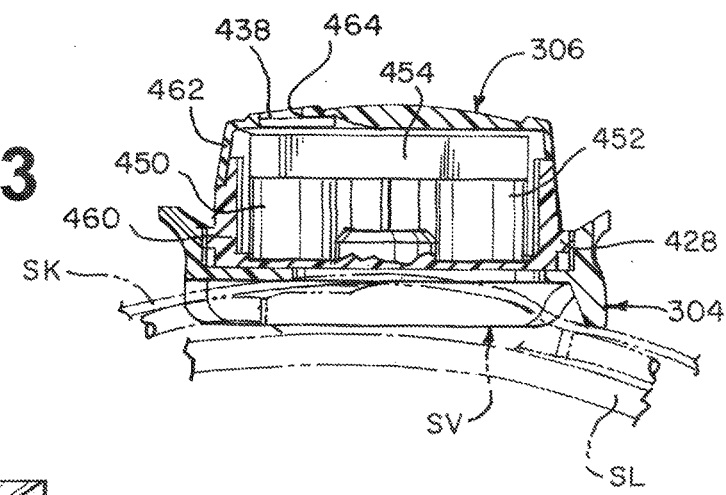
FIG. 23 is a partial cross-sectional view along lines 23-23 of FIG. 22.

The transition from the first pressure setting to the second pressure setting is illustrated in FIGS. 8 and 10 as rotor 120 is translated upwardly by magnetic attraction with an adjustment tool, such as shown in FIG. 23 below, so that rotor tooth 162 is able to clear casing lock stop 172. Cam follower 132 is shown in FIG. 8 at point 192 passing from first cam surface 191 to second cam surface 193. Lower cam section 122 has a sufficient height relative to cam follower bearing surface 235 to ensure that cam follower 132 remains in contact with a cam surface of cam portion 122 in both the constrained and unconstrained conditions. Rotor retention spring 150, FIG. 10, has been compressed, its biasing force being overcome by magnetic attraction between rotor 120 and the adjustment tool while it is positioned over valve unit 100 as shown in FIG. 23. Also illustrated in FIG. 10 are upper and lower synthetic ruby bearings 242 and 139 for upper and lower axles 136 and 138, respectively, of spring arm unit 130. Synthetic ruby bearing 240 rotatably supports rotor axle 126.

The position of the components and features within valve unit 100 at the final, "virtual off" or substantially closed setting shown in FIG. 6H is depicted at a shallower cross-sectional view in FIG. 11 in an unconstrained condition. Further clockwise rotation of rotor 120 is prevented by rotation stop or limiter 250 which projects downwardly from upper casing 104 to contact finger 127. Rotation stop 250 contacts the opposite surface of finger 127 when rotor 120 is turned fully counter-clockwise in an unconstrained condition. The actual position of rotation stop 250 may be shifted to the right of the position shown in FIG. 11 so that cam follower 132 is able to track nearly the entire portion of cam surface 205. Preferably, one side of stop 250 prevents rotor movement from the lowest setting directly to the highest setting, and also prevents the cam follower from touching the cam projection for the highest setting when the rotor is at its lowest setting. The other side of stop 250 prevents movement from the highest setting directly to the lowest setting. A side, partial cross-sectional view of rotation stop 250 blocking rotor housing 124, as well as spring 150 compressed between rotor 120 and upper casing 104, is shown in FIG. 12 for this unconstrained condition.

Further detailed views of selected features and components of rotor 120 in one construction are illustrated in FIGS. 13 and 13A. In particular, the housing portion 124 is shown as integral with cam portion 122, similar to monolithic rotor 120a of FIG. 1A. Pocket cavity 260, FIG. 13, contains magnet 123 and tantalum reference ball 129 which is readily visible during imaging of the valve unit 100 after implantation in a patient to confirm the actual pressure setting. Pocket cavity 262 holds magnet 125. A partial end view of housing portion 124 through magnet 125, pocket 262 and rotor tooth 160 is provided in FIG. 13A.

In a preferred construction, unintentional setting changes are minimized by the combination of (a) a substantially fixed, tight-tolerance, non-wobbling rotor axle, (b) abutting rotor-tooth-to-casing-stop vertical surfaces as described above, (c) a spring which biases the rotor toward the constrained condition as described above, and (d) off-axis magnets within the rotor which tend to bind the axle when a magnetic field is applied to the valve unit. In other words, it is preferable to configure the valve unit components to limit the allowable plane(s) of motion and to restrict translational movement of the rotor. The axis of magnetization of the rotor magnets preferably are arranged to lie between forty-five degrees to ninety degrees relative to the axis of rotation of the rotor, more preferably between seventy-five to eighty-five degrees. It is also preferable to orient the north and south poles of each magnet as described in more detail below.

It is desirable for the magnets 123 and 125 in the rotor 120 to be block or slot shape magnets that are magnetized through thickness, that is, each of magnets 123, 123a and 125, 125a preferably has an axis of magnetization that is perpendicular to its length and width, and is arranged with north-south polarity orientation as described in more detail below in relation to FIGS. 26A and 26B. For the construction shown in FIG. 1A, magnets 123a and 125a have BHmax of approximately 35 MGOe, with a length of 2.45 mm, a width of 1.45 mm and a thickness of 1 mm. The term BHmax refers to the maximum energy product of a magnetic material, which is the magnetic field strength at the point of full saturation of the magnetic material measured in mega gauss oersteds. Magnets 450 and 452 in a corresponding adjustment tool 306, FIG. 21, have BHmax of 42-52 MGOe, and are axially magnetized, disc shaped magnets with a diameter of 15.9 mm and a height of 15.9 mm. Suitable material, which resists demagnetization at fields up to three Tesla, for valve unit magnets includes NdFeB, and suitable material for adjustment tool magnets includes NdFeB grade 42-52. Suitable axially magnetized disc magnets 360 and 362 for an indicator tool 302, FIG. 15, have a BHmax of 42 MGOe, with a diameter of 3.18 mm and a height of 3.18 mm, and NdFeB grade 42 material.

Pressure settings for novel valve units disclosed herein preferably are noninvasively checked and adjusted using several accessories referred to as a toolset. One construction of such accessories is illustrated in FIGS. 14-23 for toolset 300 according to the present invention. An alternative construction of an indicator tool according to the present invention is shown in FIGS. 24-25 below.

Toolset 300 according to the present invention includes indicator tool 302, FIGS. 14, 15 and 18-20, a locator tool 304, FIGS. 14, 16, 17-20 and 22-23, and adjustment tool 306, FIGS. 14 and 21-23, also referred to as an adjuster tool. Indicator tool 302 and adjuster tool 306 each can nest on top of locator tool 304 as shown and described in more detail below. As illustrated in FIG. 14, toolset 300 includes in this construction a storage and transport case 308 having a smaller recess 310 for carrying adjuster 306 and a larger recess 312 for carrying indicator 302 nested with locator 304. Preferably, indicator release button 322 of indicator 302 is received within upper recess 314 when case 308 is closed for storage or transport of toolset 300.

An exploded view of components for indicator tool 302 is provided in FIG. 15. A pressure wheel assembly 359 includes a value wheel 350 supported by yoke 336, which is fixed in track 337 of wheel 350, also referred to as a readout dial. A spindle 334 rotates easily and securely on synthetic ruby bearings 332 and 338 carried by indicator housing 340 and base 370, respectively, when wheel assembly 359 is in a released or unlocked condition. Wheel 350 carries a plurality of paddles or regions, such as paddles 352 and 354 having pressure value indicia 356 and 358, respectively. Another construction having a circular disc with indicia regions is shown and described below relative to FIG. 24. Magnets 360 and 362, FIG. 15, are carried in recesses 351 and 353 of wheel 350 and preferably are fixed with a retaining compound to metal yoke 336. In one construction, yoke 336 is formed of an alloy such as Ti6Al-4V. Magnets 360 and 362 have a known north-south polarity which is oriented relative to the various value indicia on the value wheel 350 so that the proper readout will be provided when the indicator tool is placed over an implanted valve unit.

Figure 18:
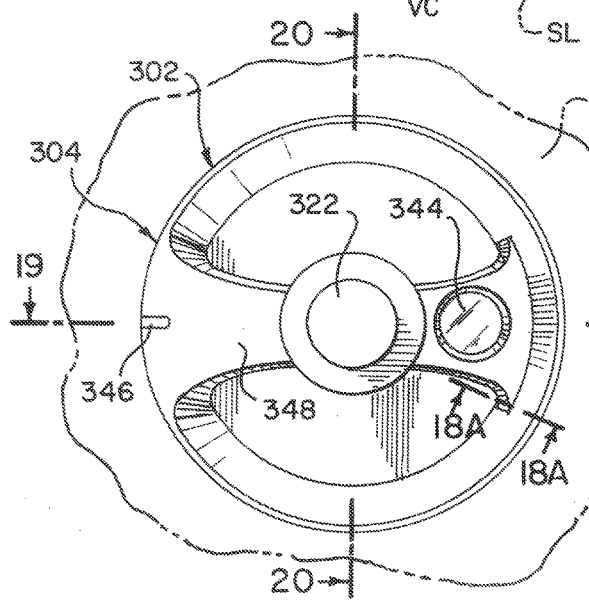
FIG. 18 is a top plan view of the indicator tool nested with the locator tool.

When release button 322 is depressed from a first position to a second position, FIG. 19A, wheel assembly 359 enters a released condition and pressure value wheel 350 is able to rotate freely on spindle 334, FIG. 15. Spring 324 biases release button 322 upwardly so that gear 330 is normally engaged in the first position by at least one catch, such as inwardly facing projections 327 and 329, formed on downward button extensions 326 and 328, respectively, at the lower portions of button 322. Gear 330 is preferably a bevel gear, more preferably a crown gear as illustrated in FIG. 15, with at least one recess between teeth or cogs, preferably a pair of opposing recesses, for each pressure indicia to be read on wheel 350. When indicator tool 302 is positioned with locator tool 304 over a valve unit, such as shown in FIGS. 18-20, wheel assembly 359, FIG. 15, rotates freely like a compass after button 322 is depressed, until a north-south polarity is encountered that is stronger than the earth's magnetic field. Unlike a compass, wheel assembly 359 preferably is able to spin and properly indicate the actual setting of a valve unit regardless of the position or orientation of the indicator tool, even when indicator tool 302 is held vertically or upside-down.

Magnets 360 and 362 of indicator tool 302 are attracted to magnets in the valve unit to be read, such as magnets 123 and 125 of valve unit 100 as shown in FIG. 13, for example. When button 322 is released, spring 324 biases it back to the first position, and projections 327 and 329, FIG. 15, travel upwardly to engage with a pair of recesses which are closest to them to drive wheel assembly 359 to the closest setting and thereby lock pressure value wheel 350 so that one pressure value is clearly visible through lens 344 carried by window or opening 342 defined in upper housing 340. Button 322 is able to translate or reciprocate along indicator axis of rotation IR but not rotate relative to indicator housing 340. Biased by spring 324, button 322 thereby drives wheel assembly 359 to a discrete pressure value position.

Figure 16:
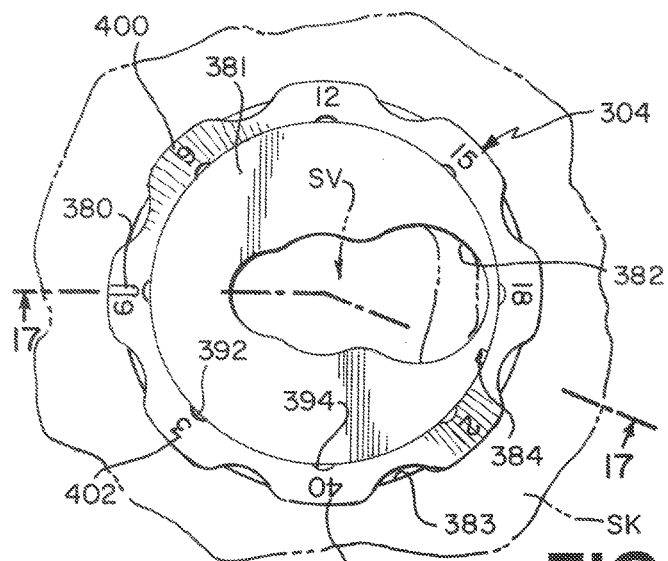
FIG. 16 is a top plan view of the locator tool of FIG. 14 positioned over an implanted valve.
Figure 18A:
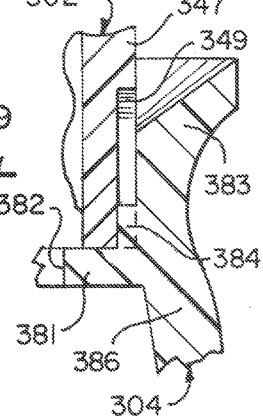
FIG. 18A is a side cross-sectional view along lines 18A-18A of FIG. 18.

Indicator tool 302 can be easily lifted by a clinician from storage case 308 by grasping raised finger grip section 348. Indicator 302 is aligned with locator 304 so that marker 346, FIGS. 15 and 18, aligns with marker 380, FIG. 16, defined on flared surface 400 of locator tool 304. In some constructions, actual rotation of indicator 302 relative to locator 304 is prevented by a key, detent or other lock feature on one tool and a corresponding recess or matching interlock on the other tool. As shown in FIGS. 16 and 18A, for example, the interior of wall 383 of locator 304 carries a projection 384, preferably a metal stop, which mates with a recess 349 in the exterior of wall 347 of indicator 302 to align the two tools in a fixed relationship.

Figure 17:
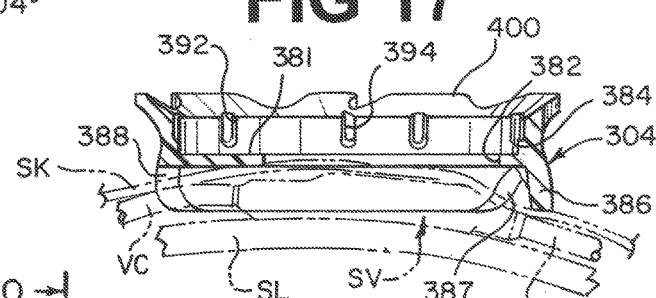
FIG. 17 is a side cross-sectional view along lines 17-17 of FIG. 16, showing in phantom the shunt valve implanted under the skin in a patient.

Locator tool 304 provides a fixed reference relative to an implanted shunt valve SV carrying a valve unit VU as shown in phantom in FIGS. 17, 19 and 20. Floor 381 of locator tool 304 defines a specially shaped upper opening 382, FIG. 16, which conforms to the implanted shunt valve SV, FIGS. 17 and 19. Additionally, lower skirt 386 of locator 304 defines openings 387 and 388 which receive distal catheter DC and ventricular catheter VC, respectively. Implanted components are shown in phantom in FIGS. 17 and 19, as are skin SK and skull SL of a patient.

Additional features on locator tool 304 are utilized with adjuster tool 306. The interior of wall 383 defines a series of reference points such as recesses 392 and 394, FIG. 16, each of which can receive a detent such as ball 426 biased by spring 424 within receptacle 422, FIGS. 21 and 22A, carried by rim 428 of adjuster 306. It is desirable to have a least one of a tactile and audible indication, such as a click sound and feel, when ball 426 engages one of the recesses 392 or 394. Also, flared surface 400 carries pressure value indicia such as lowest pressure setting 402 and highest pressure setting 404, FIG. 16, which serve as starting points for adjuster 306 as described below.

Typically, a shunt valve having a novel valve unit is initially adjusted before implantation while it is still in a sterile package. Preferably, the package has a reference indicia such as an arrow. Locator tool 304 is placed over the shunt valve so that marking 380, FIG. 16, or a marking (not shown) on the underside of floor 381, aligns with the package arrow. Indicator tool 302 is then fully seated into locator tool 304 so that indicator marking 346, FIGS. 15 and 18, is aligned with locator marking 380. Button 322 is depressed and held, such as shown in FIG. 19A, until wheel 350, also referred to as a readout dial, stops moving. Button 322 is then released. The current valve setting will be visible in indicator tool window or opening 342, through lens 344, FIG. 15. Indicator tool 302 is removed, with the current valve setting locked in position by the engagement of button projections 327 and 329 with gear 330 as described above.

While the shunt valve is still in its sterile package, adjustment tool 306 is inserted into locator tool 304 so that adjustment arrow 438 points to the valve setting number on the locator tool 304 which corresponds to the actual, current valve setting. The clinician holds the locator tool 304 with one hand and rotates adjustment tool 306 with the other hand until it points to the desired valve setting. Once the desired setting is achieved, the adjustment tool 306 is lifted straight upwards a minimum of 3 cm (1.25 inches) before any horizontal motion is imparted to it to avoid possible resetting of the valve unit. It is also desirable to have the adjustment tool 306 spaced at least 18 cm (7 inches) from the indicator tool 302 while reading the actual valve setting to avoid possible influence on the reading.

Adjustment tool 306 preferably provides an audible click and a tactile response as it is turned to each setting. Locator tool 304 defines a rotation stop, such as projection 384, FIG. 16, which prevents rotation of adjustment 306 directly from lowest setting 402 to highest setting 404, FIG. 16, or vice versa, to mimic the rotational limits on the valve rotor imposed by rotational stop 250, FIG. 11, for example. Adjustment tool 306 defines a channel 430, FIG. 21, bounded by a radially projecting arcuate stop 433 extending from edge 432 to edge 434, which allows the adjustment tool 306 to be rotated in either direction until an edge 432 or 434 of arcuate stop 433 contacts projection 380 of locator tool 304.

A similar procedure is utilized to percutaneously indicate and adjust the valve unit according to the present invention after implantation. The shunt valve is located by palpation. In one construction, the underside of floor 381, FIG. 16, of locator tool 304 carries an arrow, and that arrow is aligned with the direction of fluid flow through the implanted valve. Opening 382 of the locator tool 304 is centered around the valve unit as shown in FIG. 17. Indicator tool 302 is then placed fully into the locator tool 304 as shown in FIGS. 19 and 20 so that the markings 346 and 380 are aligned. The button 322 is depressed and held down, FIG. 19A, until the readout disc 350 stops moving. Button 322 is released and the current valve setting value is captured until button 322 is again depressed for the next reading. Indicator tool 302 then is removed.

Figure 22:
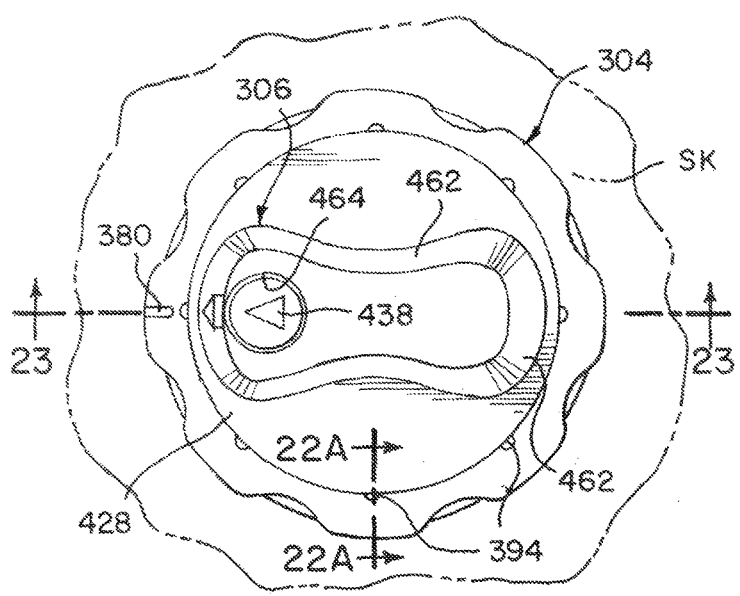
FIG. 22 is a top plan view of the adjuster tool nested with the locator tool.

Next, adjustment tool 306 is inserted into locator tool 304 as shown in FIGS. 22 and 23 so that arrow 438 is aligned with the current valve setting, which is not necessarily aligned with locator marking 380 as shown in FIG. 22. With one hand holding the locator tool 304, the clinician turns the adjustment tool 306 with the other hand until arrow 438 points to the desired valve setting. Preferably adjustment tool 306 provides an audible click and a tactile response as described above as it is turned to each setting.

After the desired setting is reached, adjustment tool 306 is lifted directly away from locator tool 304 without further rotation. Preferably, indicator tool 302 is then replaced into locator tool 304 and another reading is taken to confirm correct valve pressure setting. Alternatively or in addition to re-use of the indicator tool, the implanted valve can be imaged with x-ray to confirm current valve setting.

Figure 21:
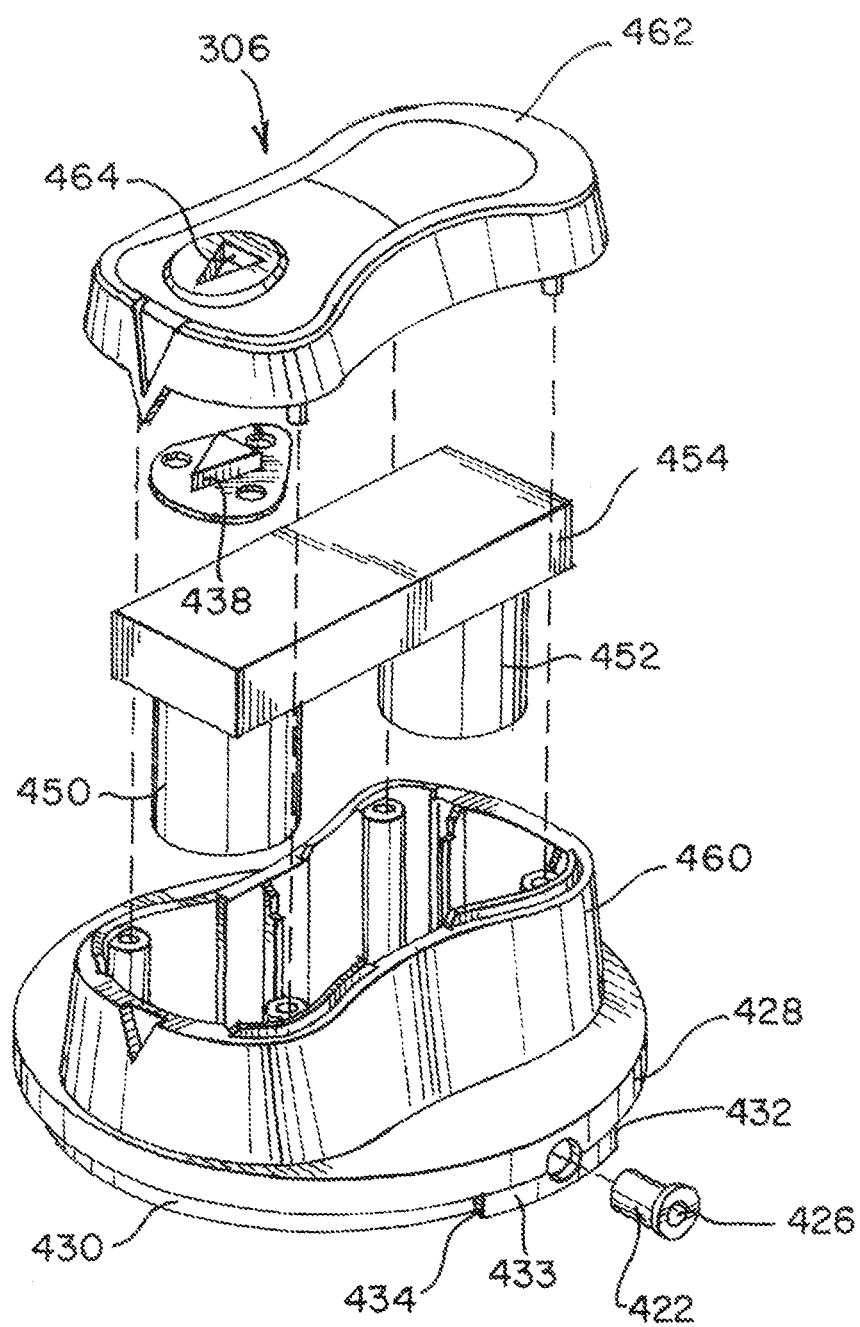
FIG. 21 is an exploded view of the setting adjuster tool of FIG. 14.
Figure 22A:
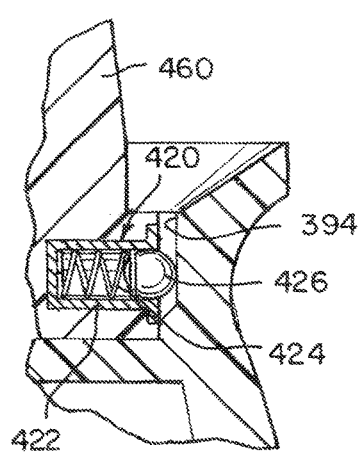
FIG. 22A is a partial cross-sectional view along lines 22A-22A of FIG. 22.

Returning to FIG. 21, components of adjustment tool 306 include a metal yoke 454, such as a bar of 416SS stainless steel, for supporting magnets 450 and 452 in a housing 460. Preferably, the poles of the magnets are aligned so that one magnet has a "north" polarity at its base while the other has an opposite, "south" polarity at its base. A cover 462 defines an opening 464 which receives arrow marker 438 in this construction as shown in FIGS. 21-23; in other constructions, marker 438 is integral with cover 462 or is applied to its surface after molding.

An alternative indicator tool 302a is illustrated in FIGS. 24-25 having a wheel assembly 359a including a circular readout dial 350a with numerical pressure value indicia such as a first, low setting 470 of "30" or "1", representing 30 mm water (294 Pa), and an eighth, high setting 472 of "400" or "8", representing 400 mm water (3,920 Pa) as a "virtual off" setting. Gear 330a is carried by metal yoke 336a, to which are attached magnets 360a and 362a, and spindle 334a, which turns freely on ruby bearings 332a and 338a supported by shims 474 and 476, respectively, when button 322a is depressed against the biasing force of spring 324a to move from a first, locked position to a second, released position.

Stops 480 and 482 of button 322a are catches that are shown engaging horizontal teeth of gear 330a in FIGS. 24 and 25 in the normal condition for indicator tool 302a. Also shown are housing bottom 370a and lens 344a carried in upper housing 340a.

Yet another alternative construction of an indicator tool according to the present invention is shown in FIG. 26 nested in a locator tool 500 defining an opening 502 in a floor 504. Indicator tool 510 has a wheel assembly 512 which includes readout dial 514 with performance setting indicia, metal yoke 516, first crown gear 522 fixed to an upper surface of yoke 516, magnets 518 and 520 mounted on a lower surface of yoke 516, all rotatable on bearing 517 mounted on platform 524 of indicator housing lower portion 534. Release button 530 has an enlarged head 531 at a lower end and has a second crown gear 532, serving as a catch when button 530 is in a first position, mounted by press fit at a middle axle section of button 530. An upper end of button 530 has a narrowed key element 533 which is movable vertically within slot 537 defined by indicator housing upper portion 538. Rotation of button 530 is prevented by the interaction of key element 533 with the side walls of slot 537. Bearing 517 enables translational, thrust movement of button 530 as well as enabling rotation of wheel assembly 512.

In this construction, the act of nesting indicator tool 510 into locator 500 causes a portion of head 531 of release button 530 to contact a portion of locator floor 504, near opening 502, which overcomes the downward bias provided by coil spring 540 to move button 530 from a first, normally locked position to a second, rotatable position as illustrated in FIG. 26. The act of removing indicator tool 510 from locator tool 500 allows spring 540 to automatically drive second, catch gear 532 downward to mesh with first gear 522 of wheel assembly 512. One of the performance setting indicia on dial 514 is then readable through magnifying lens 528 to record the actual setting of a valve unit.

Figure 27B:
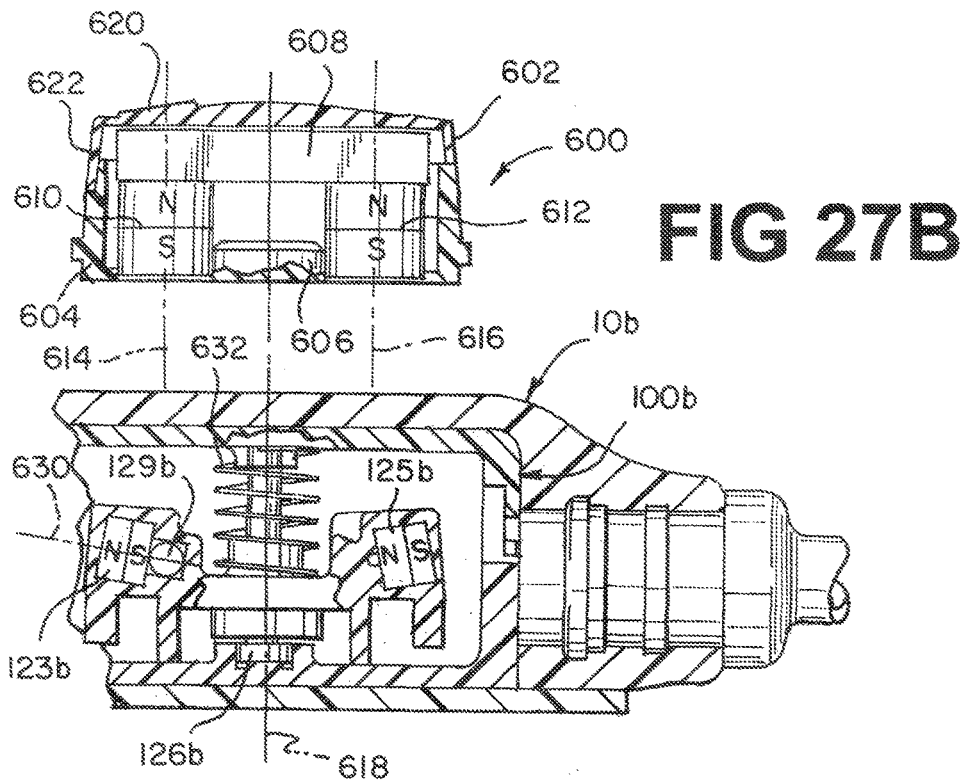
FIG. 27B is a schematic cross-sectional view along lines 27B-27B of FIG. 27A showing only the adjuster tool and a portion of the shunt valve with valve unit, shown at 10X scale.
Figure 28:
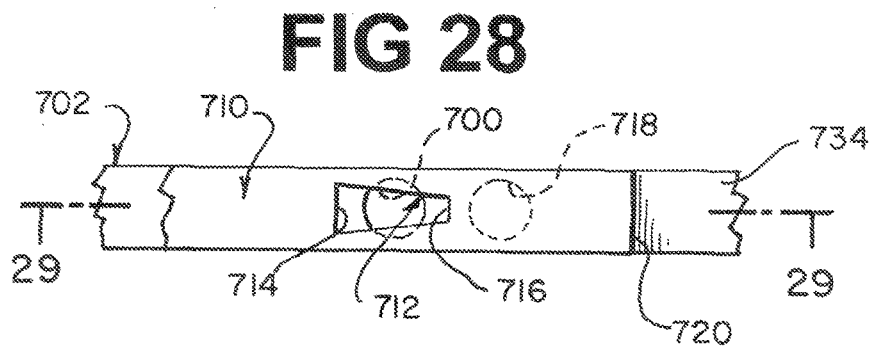
FIG. 28 is a schematic side view of the distal portion of an alternative movable valve member with a port restricting element to control flow of bodily fluid.
Figure 29:
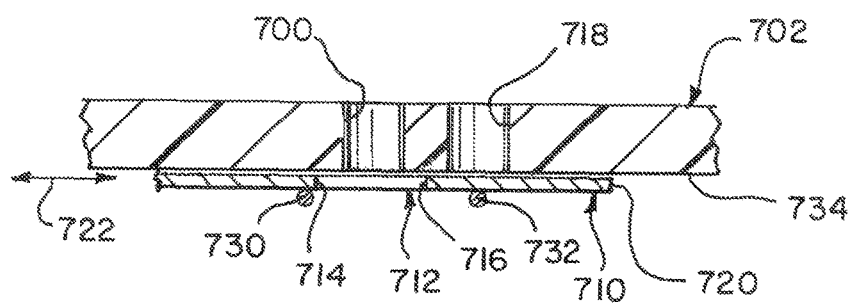
FIG. 29 is a partial top cross-sectional view along lines 29-29 of FIG. 28.

An alternative adjuster tool 600 is shown in FIGS. 27A and 27B positioned over skin SK of a patient P with an implanted shunt valve 10b having a valve unit 100b, which is similar in construction to shunt valve 10a with valve unit 100a as shown and described above relative to FIG. 1A. A locator tool as described above has been omitted from these drawings, and everything other than a portion of shunt valve 10b, at a scale of approximately 10× relative to adjuster tool 600, has been omitted from FIG. 27B for clarity in discussing orientation of magnetic polarities and axes of magnetization.

Adjuster tool 600 has an upper housing 602 and a lower housing 604 with an enlarged floor portion 606 to assist securing magnets 610 and 612 in position. Upper casing 602 has an integral directional arrow 620 for proper alignment with a locator tool and has a marker 622 which confirms directional alignment of upper casing 602 with lower casing 604 during assembly.

Adjuster magnets 610 and 612 are connected by metal yoke 608 and each has an axis of magnetization 614 and 616, respectively, which are substantially parallel in this construction as indicated with dashed lines. During adjustment of a valve unit according to the present invention such as valve unit 100b, axes of magnetization 614 and 616 are oriented to be substantially parallel to axis of rotation 618 through axle 126b of rotor 120b. In this construction, adjuster magnet 610 has a south pole S that is oriented to face rotor magnet 123b and imaging reference ball 129b while north pole N of magnet 612 is oriented to face rotor magnet 125b. Rotor 120b is shown in a constrained condition in FIG. 27B, and is lifted to an unconstrained condition when the lower surface of adjuster tool 600 approaches within three cm (less than 1.25 inches) of the floor of a locator tool positioned on skin SK, FIG. 27A.

Axis of magnetization 630 of rotor magnet 123b is shown having an angle 632 relative to axis of rotation 618, with north pole N facing radially outwardly relative to axis of rotation 618. Rotor magnet 125b has a similar axis of magnetization, but with south pole S facing radially outwardly away from axis of rotation 618. Angle 632 is approximately eighty degrees in this construction. While an angle of ninety degrees from axis of rotation 618 for the axes of magnetization for rotor magnets 123b and 125b may be most effective for detection of actual setting by an indicator tool according to the present invention, it has been found that offset angles of seventy-five to eighty-five degrees, most preferably approximately eighty degrees, are suitable for interaction with the adjustment tool 600. Further, having axes of magnetization other than zero degrees and ninety degrees reduces the likelihood of simultaneous de-magnetization of both rotor magnets when exposed to a magnetic field greater than 3 Tesla or other large electromagnetic field. In other words, it is preferable for the axes of magnetization of the rotor magnets to be offset relative to each other instead of parallel to each other to resist de-magnetization as well as to encourage binding of axle 126b when exposed to unintended magnetic fields.

Instead of controlling opening pressure as described above, the rate of flow of a bodily fluid can be controlled using adjustable performance settings to regulate passage of the bodily fluid. A port 700, FIGS. 28 and 29, such as an inlet or an outlet for the bodily fluid in a casing 702, has a valve mechanism of a spring arm unit positioned at the port. The valve mechanism includes a movable valve member such as member 710. Only the distal portion of valve member 710 is shown, terminating in distal end 720. A spring arm unit, otherwise substantially similar to configurations described above, has a cam follower arm in slidable contact with the cam surfaces of a rotor and has a resilient spring element applying a closing effect with the valve member 710 at the port 700 to establish a flow control setting as the performance setting for the valve unit. Sufficient rotation of the rotor to change the cam surface in contact with the cam follower alters the closing effect with which the valve member moves relative to the port, such as by imparting a sliding action indicated by arrow 722, FIG. 29 as the spring arm unit pivots, and thereby alters the performance setting of the valve unit in a linear or non-linear manner as desired.

In this construction, movable valve member 710 is integral with the resilient spring element and defines a non-linear orifice 712 having a wide edge 714 and a narrow edge 716. A closed region 718 provides a substantially closed, minimal-flow setting. Fixed guides 730 and 732, FIG. 29, maintain the valve member 710 proximate to inner surface 734 of casing 702.

The distal end of another construction of a movable valve member 710a for controlling flow is illustrated in side view in FIG. 30. An initial section 740 is linear. Member 710a then increases in height beginning at point 742 until a maximum height is reached at point 744 to provide progressive restriction of a port as member 710a is moved in the direction of arrow 748. A closed region 746 preferably is larger in height than the diameter of a port to be closed, such as an inlet or an outlet to a housing.

In many circumstances, more accurate positioning of a tool set relative to an implanted programmable valve or other adjustable device can be accomplished by determining both the location and orientation of the implant. It is desirable to decrease reliance on the accuracy of a user while positioning the tool set and to increase the likelihood of accurate indication of actual performance setting of the implant. Positioning tools and methods according to the present invention guide a user towards appropriate positioning of tools to more accurately indicate and adjust the setting of an adjustable implant such as a programmable shunt valve device.

Figure 33:
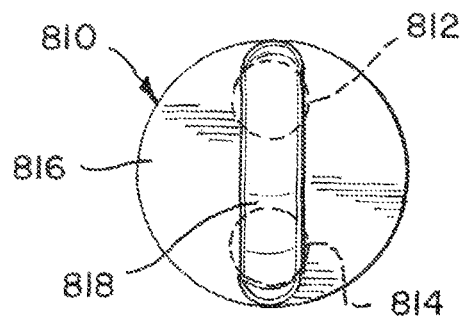
FIGS. 33 and 33A are schematic top and side views of an adjustment tool for use with the positioning tools of FIGS. 31 and 32.
Figure 33A:
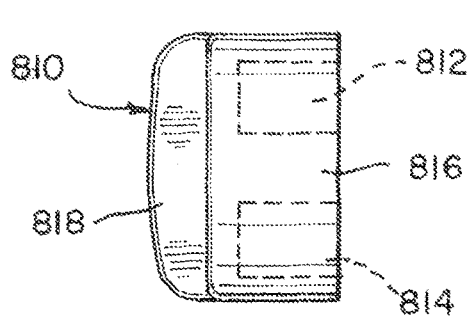

A positioning tool 800 according to the present invention is shown in FIGS. 31 and 31A having a body 802 defining a centrally located access hole 804, intended to be directly positioned over the implant with bottom surface 801 resting against the skin of a patient, into which fits an adjustment tool 810, FIGS. 33 and 33A, having a body 816 and a handle 818 suitable for gripping by a thumb and a finger of a user wearing gloves, or between two gloved fingers of the user, to enable manipulation of adjustment tool 810 as described in more detail below.

Preferably, mechanical interference between the dimensions of the hole 804 and the adjustment tool 810, which in some constructions is enhanced by a rib, a ridge, or another feature on the periphery of at least one of the hole 804 and body 816 of adjustment tool 810, would limit the inward travel of the adjustment tool 810 to minimize or avoid protrusion beneath the positioning tool 800. It is also desirable to maintain alignment of the adjustment tool 810 if the implant were to protrude into the hole 804 to bring the patient's skin in contact with the adjustment tool 810.

The positioning tool 800 also defines a storage cavity 806 to hold the adjustment tool 810 and, preferably, with a material such as nickel iron alloy to contain, that is, to absorb and redirect, the magnetic flux emanating from the magnets 812 and 814 within body 816 while adjustment tool 810 is not being utilized. This storage, preferably with shielding, is intended as a safe place for the magnets 812 and 814, so that they do not interfere with the magnetic field sensing capability of the positioning tool 800, which is described in more detail below. The terms "magnet" and "magnets" as utilized herein include metals and alloys having properties of attracting or repelling iron as well as electromechanical mechanisms for generating similar magnetic fields.

Positioning tool 800 includes a display 803 in this construction to enable the user to select the mode of operation and to provide visual feedback to the user. Also included is a power button 805 and a selection button 807 to enable the user to navigate the through menu driven options. Internal circuitry and an energy source such as a battery are also contained within body 802 in this construction. One technique for operating positioning tool 800 is described below in relation to FIGS. 35-39.

An alternative positioning tool 820, FIGS. 32 and 32A includes a moveable bezel 822 with the numbers 1 through 8 corresponding to the implant settings, an indicator mark 824 on setting #2, and indications 826 of degrees on body 828 of tool 820, shown in FIG. 32 in five degree increments from zero to twenty degrees. These could be used in an optimize tool orientation method described below as an alternative procedure in relation to FIGS. 38-39, where the $1^{st}$ & $2^{nd}$ RC (Rotational Construct, also referred to as a rotor) orientations have been found and then utilized to calculate how far out of orientation the tool is, where this number is delivered to the user so that the bezel 822 can be adjusted, such as by manual rotation, to achieve proper orientation. As one example, the user moves the bezel 822 so the mark 824 on the center of setting 2 is at the 5 degrees mark on body 828. The body 828 further defines an access hole 830, an adjustment tool storage recess 832, a power button 834, a display 836, and a mode selection button 838 in this construction.

Figure 34:
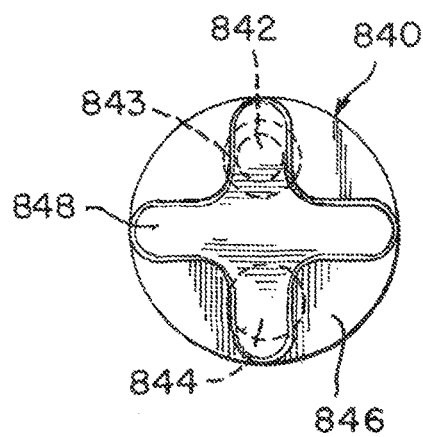
FIGS. 34 and 34A are schematic top and side views of an alternative adjustment tool for use with the positioning tool of FIG. 32.
Figure 34A:
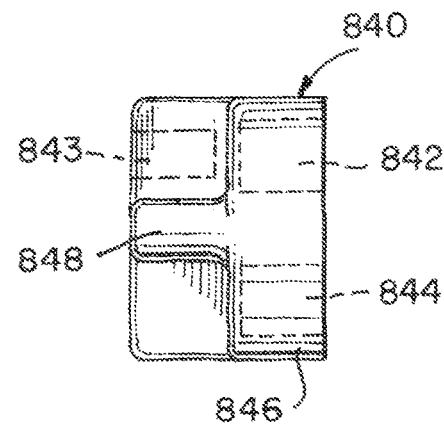

An adjustment tool 840, FIGS. 34-34A, includes an additional magnet 843, located in handle 848 on the opposite end to magnets 842 and 844 within body 846, to facilitate moving the RC during the process described below in relation to FIGS. 38-39 wherein the adjustment tool 840 is inverted and rotated, while exposing the single pole magnetic field of magnet 843 to the implant. Recess 832 is sufficiently deep, as shown in FIG. 32A, to store adjustment tool 840 and, preferably, contain (absorb and redirect) magnetic flux so as to shield the magnetic field of adjustment tool 840 from other components of positioning tool 820.

Figure 35:
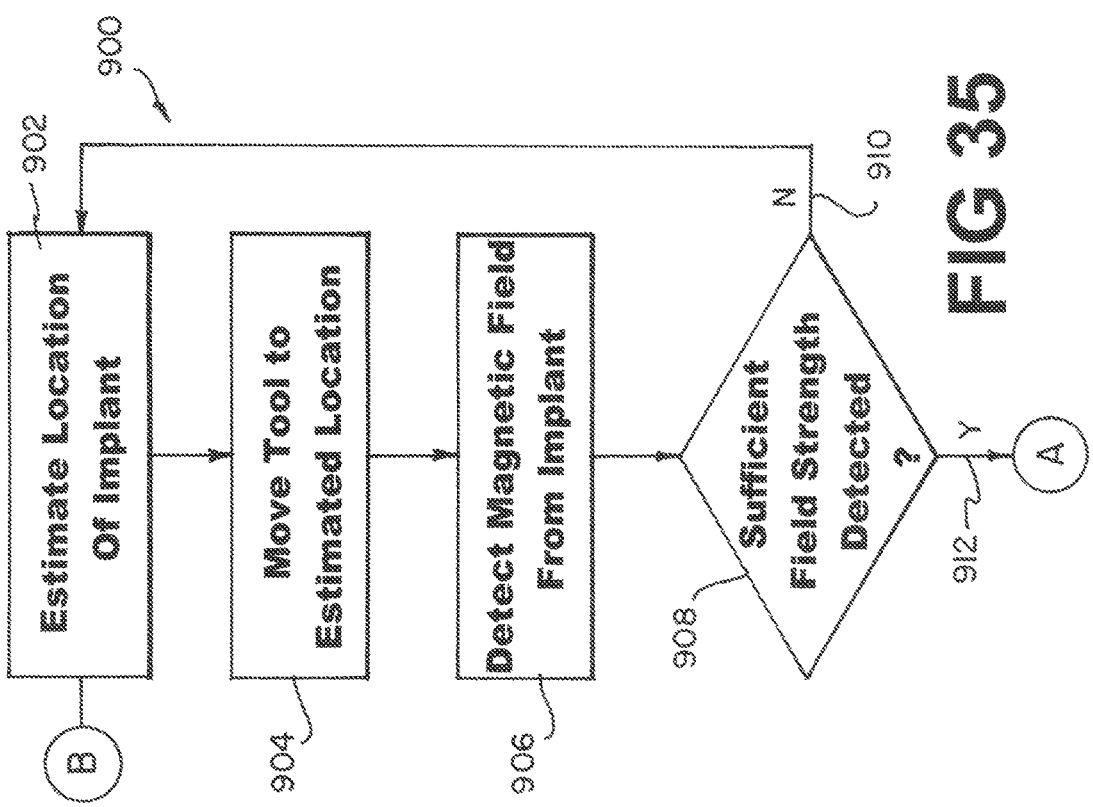
FIGS. 35 and 36 are flow charts showing one technique according to the present invention to optimize tool location.
Figure 36:
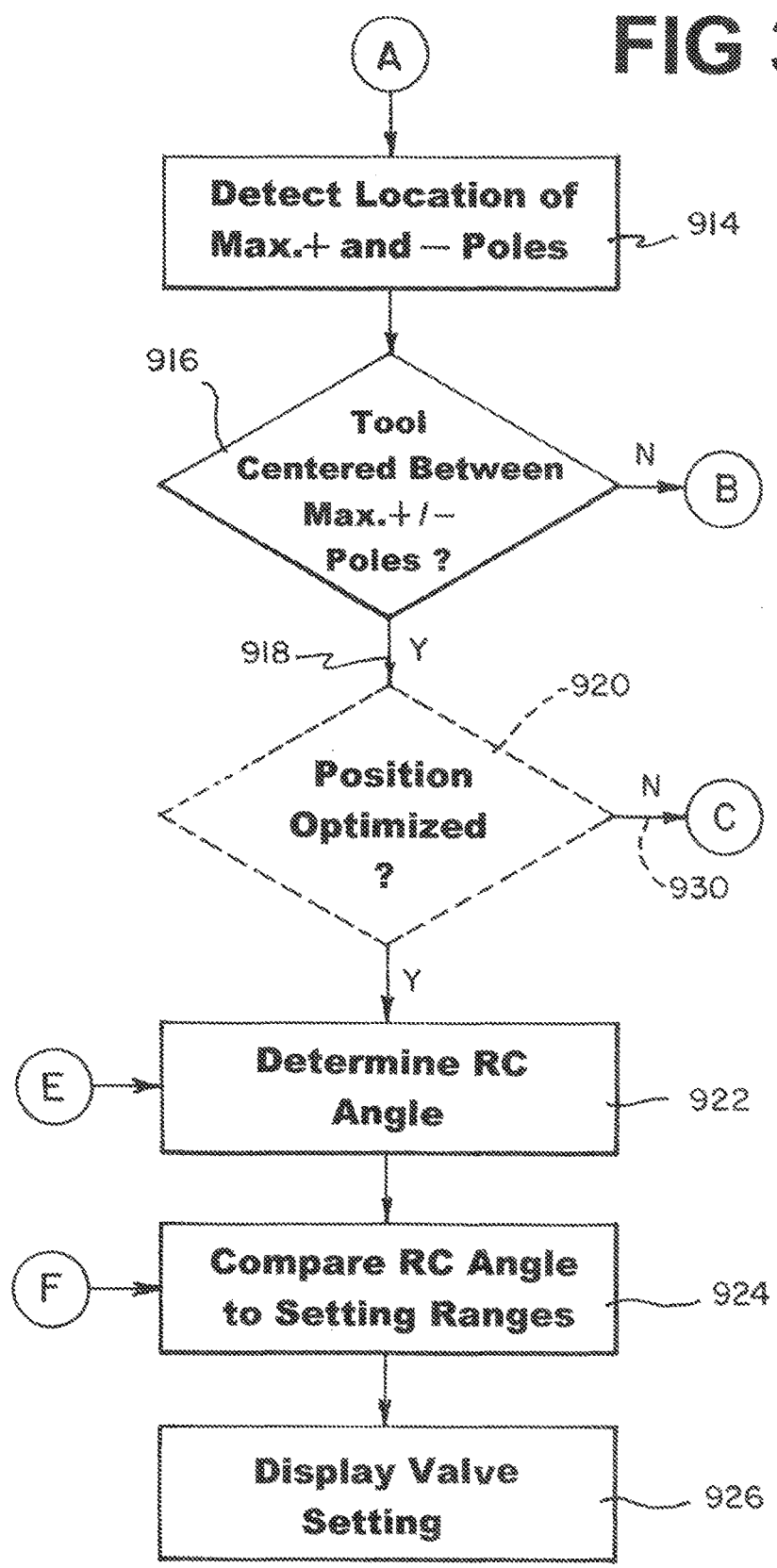

Several techniques to optimize tool location and position are illustrated in FIGS. 35-39. FIGS. 35 and 36 are flow charts showing a technique 900 according to the present invention to optimize tool location. A user estimates, step 902, the location of an implant such as a programmable valve, such as by palpation, and places, step 904, a positioning tool according to the present invention at the approximate location of the implant. The user orients the tool relative to the approximated longitudinal axis of the valve, that is, in the direction of flow through the implanted valve. Next the user selects and initiates active magnetic field detection, step 906, utilizing the positioning tool, wherein the tool first confirms that sufficient field strength is detected, step 908. If not, the logic returns to step 902, providing audio and/or visual guidance to the user such as via displays 803 or 836, FIGS. 31 and 32, respectively. One type of sensor array to accomplish magnetic field detection is described below in relation to FIG. 40.

Once sufficient field strength is confirmed in step 908, FIG. 35, in one construction the logic proceeds, line 912 to circled A, to detect the location of the maximum positive and negative poles, step 914, FIG. 36. The display actively provides visual and/or audio feedback, step 916, with return to estimating the location of the implant as shown by circled B to step 902, as the user moves the position of the tool until the tool senses that it is concentric with the implant, line 918. An optional "position optimized?" step 920, shown in phantom, is discussed below.

In one procedure, the tool next determines the implant setting by determining, step 922, and comparing, step 924, the RC angle, that is, the angle between the user-approximated direction of flow and the line that passes through the detected maximum positive and negative peaks from the magnets in the RC, versus a lookup table that has ranges for each implant setting based on perfect direction of flow.

Figure 37:
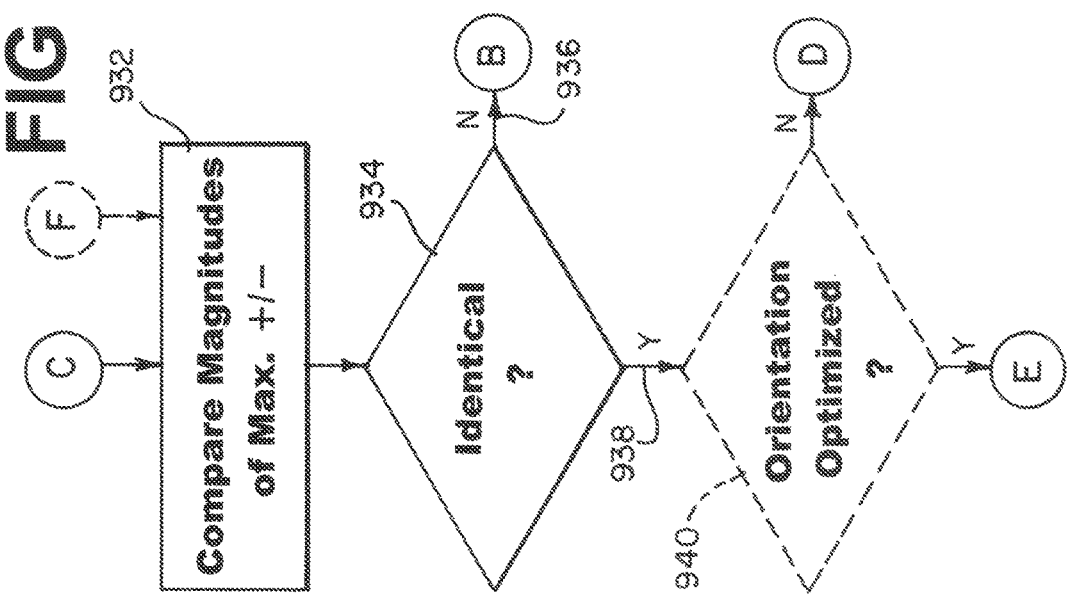
FIG. 37 is a flow chart illustrating optimization of tool position such as by changing roll or pitch of the tool.

FIG. 37 is a flow chart illustrating optimization of tool position, represented by optional step 920, FIG. 36, such as by changing roll or pitch of the tool. The user first optimizes the tool location, steps 902 to 916 as described above. The tool is then utilized, line 930 to circled C proceeding to step 932, FIG. 37, to compare the magnitude of the maximum positive and negative peaks, wherein the field from the identical implant magnets should be detected as identical, step 934, when the tool is placed parallel to the implant. The tool display would convey to the user the detected imbalance in vector form, and this would actively change as the user manipulates the roll and pitch of the tool, the logic returning via line 936 to circled B to step 902, FIG. 35, with the goal to achieve no visual vector of imbalance, line 938 to circled E, FIG. 37, proceeding to step 922, FIG. 36.

Figure 38:
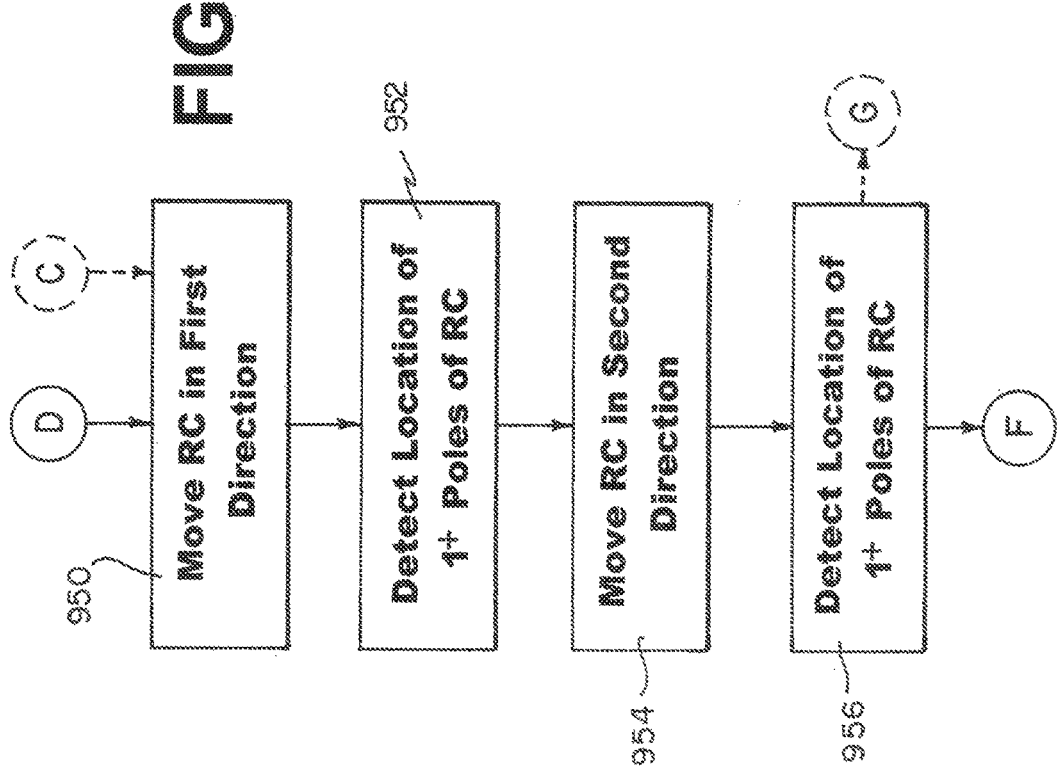
FIG. 38 is a flow chart showing optimization of tool orientation.
Figure 43:
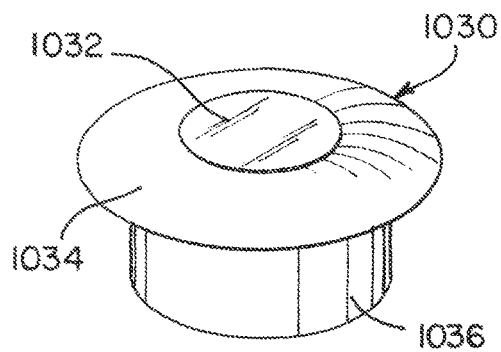
FIG. 43 is a schematic perspective view of an alternative detection tool of an additional positioning toolset according to the present invention.
Figure 44:
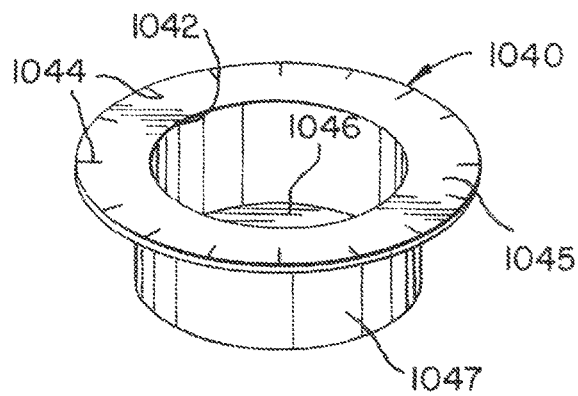
FIG. 44 is a schematic perspective view of an alternative locator tool according to the present invention.

FIG. 38 is a flow chart showing details for optional optimization of tool orientation, step 940, FIG. 37, such as by detecting yaw relative to a programmable implant having "setting pockets", also referred to as "pockets", such as the first space or pocket established between lock stops 170 and 172, FIG. 6A, for a first performance setting and the second space or pocket established between lock stops 172 and 174, FIG. 6B, for a second performance setting, wherein an RC such as a rotor can move within each pocket without changing the performance setting. In this construction the user magnetically moves, step 950 in FIG. 38, the implant RC to one end of the setting pocket, the tool detects the RC angle, step 952, and then the user repeats the move, step 954, for the opposite end of that pocket for the same setting, step 956. In one construction, the maximum angular range of RC movement within a pocket is approximately 34 degrees for an implant having eight performance settings. One specialized tool for accomplishing the "pocket check" range of RC movement is adjustment tool 840, FIGS. 34-34A, with additional "checking" single magnet 843 as described above. In other words, while two magnets are preferred to lift the RC and shift it to a different pocket, only a single "checking" magnet is needed for a "pocket check" to confirm the actual pocket that the RC is occupying. Additionally, a "checking" magnet having an opposite polarity is desired to attract the closest RC magnet instead of trying to repel the RC magnet during the pocket check. In another construction, one or more "checking" magnets are located within a tool that automatically and sequentially attracts the RC to the angular limits of the setting pocket.

In one procedure, the logic proceeds to circled F and to step 924, FIG. 36, with a more accurate valve setting displayed, step 926. The angular range-of-movement window described by the two arcuate ends of the pocket is information that, when compared to a lookup table, step 924, would significantly increase the level of confidence of the reported implant setting. In other words, with only a single RC angle that is near the border between two settings, an incorrect determination can more easily be made than in the case where an RC window (formed by two angles) is provided, that is smaller than the setting window, so that simply the largest percent of the RC window that resides in any particular implant setting window determines the Implant setting.

For example, if the tool detects a field that is 37 degrees relative to the assumed longitudinal axis of the implant, it could be interpreted as either setting #2 or setting #3. However, when the RC is moved to the extremes of rotational travel within a pocket, without changing the performance setting of the implant, if the detected field ranges from 35 degrees to 62 degrees, the implant must be at setting #2. By comparison, if the detected field ranges from 15 degrees to 38 degrees, it must be at setting #3. Neither precise positioning of the tool nor repositioning of the tool for the purpose of setting indication is necessary, unless gross miss-positioning of the tool is detected.

In another construction, the logic proceeds from step 920, FIG. 36, directly to step 950, FIG. 38, as shown by the dash-circled C at the top of FIG. 38. In yet another construction, the logic proceeds from step 956, FIG. 38, to step 932, FIG. 37, as shown by the dash-circled F at the top of FIG. 37.

Figure 39:
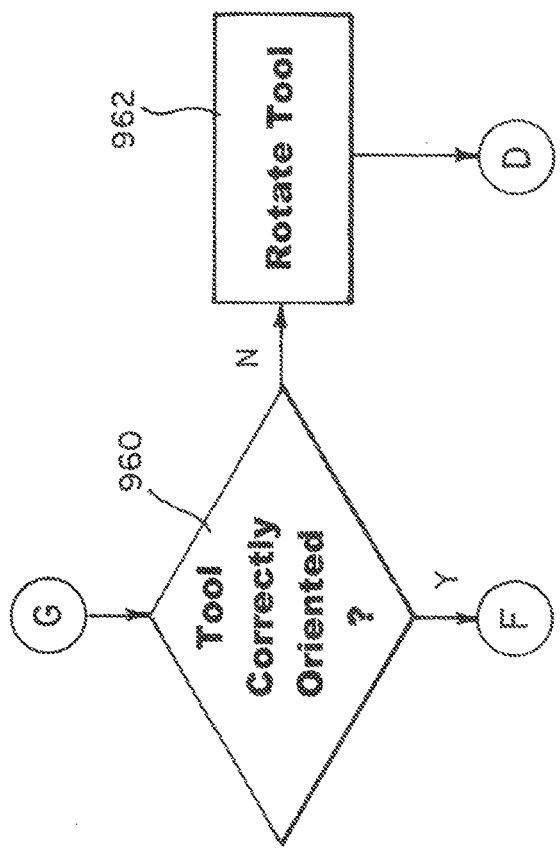
FIG. 39 is a flow chart showing optional further steps to optimize tool orientation.

FIG. 39 is a flow chart showing optional further steps from step 956, FIG. 38, via dash-circled letter G to step 960, FIG. 39, to optimize tool orientation by moving all or a portion of a tool. In addition to greater confidence in the setting reading, this method can be used to provide feedback to the user to correct the tool yaw. Improved tool yaw ensures that, during the adjustment of the implant, the adjustment magnet properly de-couples with the RC when it is positioned in the center of the pocket, so that it can drop in the correct setting pocket and enter the 'locked' position immediately. The feedback, step 960, can be in a manner similar to the Optimize Tool Location method of FIGS. 35-36, wherein the user rotates the tool, step 962, until, for example, a visible seconds hand reaches 12 o'clock position. After each rotation of the tool or a portion thereof, such as by holding the bezel 822 in position while moving the tool body 828, FIG. 32, or by moving only the bezel as described below, the logic proceeds as shown by circled D to step 950, FIG. 38. When the tool is correctly oriented, step 960, the logic proceeds as shown by circled F to step 924, FIG. 36.

Alternatively the display provides a numerical output to the user that references markings on the positioning tool and markings on a rotatable bezel. For example, if the tool is intended to be oriented such that the longitudinal axis of the tool is aligned with the direction of flow through the implant, then the setting #2 should be at approximately 6 o'clock. In FIG. 32, the moveable bezel 822 has a mark 824 for the center of setting #2, and the tool 820 has angular increments 826. Here the display 836 can convey to the user that, based on the detected RC window, the current orientation of the bezel should be rotated to align the mark at setting #2 with some value in degrees on the Tool, to correct the yaw of the bezel, where the bezel will dictate the position of the adjustment magnet upon completion of the implant setting change procedure.

FIG. 40 is a schematic diagram of three sensor arrays 1002, 1004 and 1006 for a positioning tool 1000 according to the present invention, each array sensing three different axes (a) X, Y, Z, (b) X', Y', Z' and (c) X", Y" and Z", respectively. In one construction, each array 1002, 1004 and 1006 has three Hall effect sensors, each sensor arranged along an axis different from that of the other sensors. In other constructions, each array has one, two, or differing numbers of sensors. Working together, the sensor arrays preferably are able to detect the magnetic field midpoint between the north and south poles of the RC (Rotational Construct) of the implanted programmable valve, as well as the relative direction of the field, or axis of the field, in three-dimensional space. This information is then utilized to direct the user to best position the locator and/or indicator tools relative to the implanted valve.

Figure 41A:
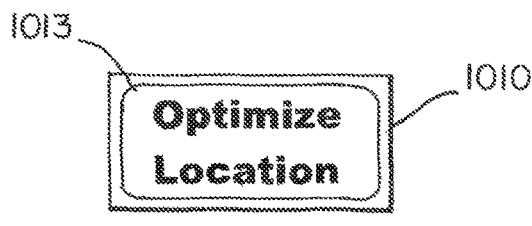
FIGS. 41A and 41B are examples of displayed mode and guidance to a user, respectively, for the display screens shown in FIGS. 31 and 32.
Figure 41B:
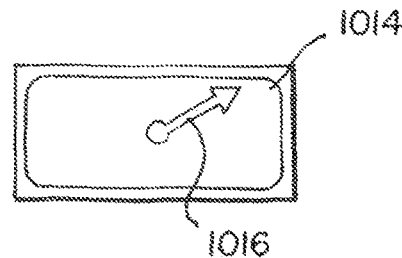

FIGS. 41A and 41B are examples of displayed mode and guidance to a user, respectively, such as for the display screens shown in FIGS. 31 and 32. Screen 1010, FIG. 41A, displays message 1013 stating "OPTIMIZE LOCATION" to indentify the selected mode, such as the mode depicted in FIGS. 35-36. Screen 1014, FIG. 41B, displays a directional arrow 1016 to guide the user to move the tool in the indicated direction. In one construction, arrow 1016 is a vector-type arrow in which the amount of distance to be traveled is depicted by the length or other magnitude of arrow 1016.

FIGS. 42A-42C are top views of alternative displays 1024 guiding a user utilizing indicator tool 1020 which, in one construction, is positioned within a locator tool 1022. The centered dot or small circle 1026a, FIG. 42A, depicts the desired centered, concentric location over the implanted valve, as represented by dashed oval or lozenge-shaped image 1028a. Arrow 1026b, FIG. 42B, indicates movement needed to achieve centering over the implanted valve, represented by image 1028b. Similarly, arrow 1026c, FIG. 42C, provides another example of the direction a user should move the indicator and/or locator tools to achieve an optimum location relative to image 1028c.

Magnetic detection of an implanted valve is limited both by the quality of the sensing capabilities of the detection tool as well as by the proximity to the implanted valve that is afforded to the sensors of the tool. Limiting how close the sensors can be positioned relative to each other and to the implanted valve can result in less than optimum setting indication and adjustment. Additionally, exposure of sensors to a significant magnetic field can affect the performance of the sensors, to the extent that additional steps must be performed to re-zero or re-calibrate the sensors.

Several constructions of an improved positioning toolset according to the present invention have an indicator tool which is also referred to as a detection tool, one or more locator features such as a separate locator tool or integral locator elements, and an adjustment tool which, in some constructions, also has locator elements. The detection tool electronically senses the location of the implanted valve and provides feedback to the user to optimize the position of the tool relative to the implanted valve. The detection tool is capable of detecting the valve setting based on the direction of the magnetic field detected, instead of relying on the orientation of the tool as positioned by the user based on an estimate of valve orientation.

The locator feature utilizes the optimized location from the detection tool to establish the same optimal position for subsequent placement of the adjustment tool. In one construction, a detection tool 1030 according to the present invention, FIG. 43, having a liquid crystal or light-emitting diode display 1032 within a rim 1034 above a body 1036, is placed into opening 1042 of a separate locator tool 1040, FIG. 44, having markings 1044 on a rim 1045 above a body 1047, and a floor 1046 preferably having an implant-shaped cutout as described above.

Detection tool 1030 nested within locator tool 1040 is placed upon the patient in the vicinity of the implanted valve. A user is then prompted visually via display 1032 and/or by audio commands generated by tool 1030 to move the position of the nested tools to achieve an optimal location directly above the implanted valve, such as described above in relation to FIGS. 35-39. Once an optimum position is achieved, detection tool 1030 indicates the actual setting of the valve, and then detection tool 1030 is removed while locator tool 1040 is kept in position.

Figure 45:
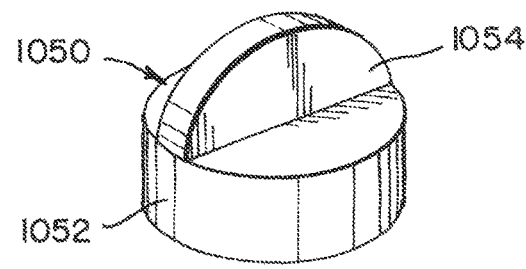
FIG. 45 is a schematic perspective view of an alternative adjustment tool according to the present invention.
Figure 46:
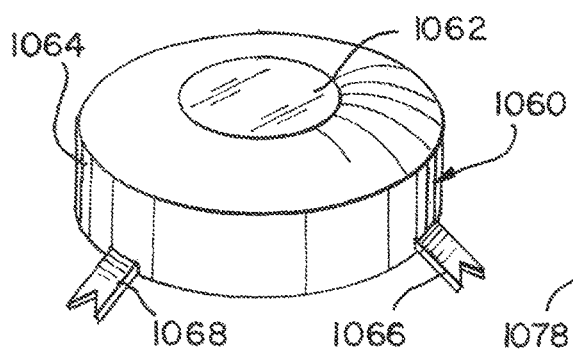
FIG. 46 is a schematic perspective view of yet another detection tool according to the present invention with marking guides.

An adjustment tool 1050, FIG. 45, having a body 1052 containing one or more magnets and having a handle 1054, is then nested within the locator tool 1040 and utilized as described above to alter the valve setting as desired. Markings 1044 on rim 1045 guide the user during rotation of the adjustment tool 1050 to the desired setting. Confirmation of the valve setting change can be performed by exchanging the adjustment tool 1050 with the detection tool 1030 while maintaining locator tool 1040 in the same position, or by removing both the locator tool 1040 and the adjustment tool 1050 before returning detection tool 1030 to that position on the patient.

Another construction of an improved toolset according to the present invention has a detection tool with integral external locator features, and an adjustment tool with similar external locator features. Detection tool 1060, FIG. 46, has a display 1062 within a body 1064 and marking guides 1066 and 1068 which are placed in proximity to the skin of a patient. A user follows prompts from detection tool 1060 to achieve an optimal location directly above an implanted valve, and then display generates an audio and/or visual indication of current valve setting. A standard pen or skin marker is then utilized by a user to create visible marks on the patient using marking guides 1066 and 1068 for reference. Detection tool 1060 is then removed.

Figure 47:
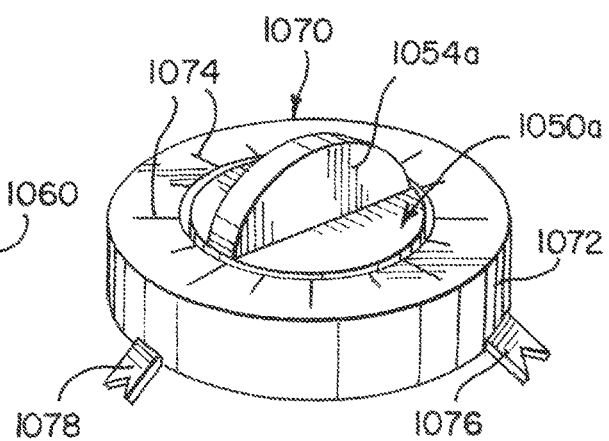
FIG. 47 is a schematic perspective view of yet another adjustment tool according to the present invention with marking guides similar to those of FIG. 46.

An adjustment tool 1070, FIG. 47, is then positioned on the patient to align marking guides 1076 and 1078 on body 1072 with the visible marks on the patient. Adjustment member 1050*a* with handle 1054*a* and internal magnets is then rotated within body 1072 to change valve setting as desired with reference to markings 1074 on body 1072, which is held stationary. Confirmation of correct valve setting can be performed by exchanging detection tool 1060 for adjustment tool 1070 using the visible marks on the patient for reference.

As will be readily apparent from the above description, independent detection and adjustment tools according to one aspect of the present invention enables the detection tool to be smaller, simpler, and generally isolated from magnets within the adjustment tool. This eliminates the need to re-zero sensors within the detection tool that would otherwise occur if the detection tool was exposed to one or more magnetic fields of the adjustment tool. In some constructions, sensors can be placed closer together within the detection tool to enable more precise detection of the magnetic field of one or more magnets associated with the implant. In certain constructions, instead of Hall effect sensors, one or more sensor arrays are an array of other types of magnet field sensors, including purpose-built sensors, capable of detecting the three-dimensional orientation of a magnetic field. In a number of constructions, the array is a solid state component incorporating multiple single- or multi-plane magnetic field detectors.

Thus, while there have been shown, described, and pointed out fundamental novel features of the invention as applied to a preferred embodiment thereof, it will be understood that various omissions, substitutions, and changes in the form and details of the devices illustrated, and in their operation, may be made by those skilled in the art without departing from the spirit and scope of the invention. For example, it is expressly intended that all combinations of those elements and/or steps that perform substantially the same function, in substantially the same way, to achieve the same results be within the scope of the invention. Substitutions of elements from one described embodiment to another are also fully intended and contemplated. It is also to be understood that the drawings are not necessarily drawn to scale, but that they are merely conceptual in nature. It is the intention, therefore, to be limited only as indicated by the scope of the claims appended hereto.

Every issued patent, pending patent application, publication, journal article, book or any other reference cited herein is each incorporated by reference in their entirety.

What is claimed is:

1. A valve unit capable of being implanted in a patient and having adjustable performance settings to regulate passage of a bodily fluid, comprising:
   a casing defining a port for the bodily fluid;
   a valve mechanism positioned at the port and including a movable valve member;
   a rotor disposed at a first location in the casing and having an axle which rotates about an axis of rotation, the rotor is also movable along the axis of rotation from a constrained condition, in which the rotor is constrained to rotate in an arc of predetermined angular distance, to an unconstrained condition; and
   a spring arm unit disposed at a second location in the casing having a cam follower arm in slidable contact with the rotor and having a resilient spring element applying a closing effect with the movable valve member at the port to establish a performance setting for the valve unit;
   wherein sufficient rotation of the rotor alters the closing effect with which the valve member moves relative to the port, and thereby alters the performance setting of the valve unit;
   the casing defines a plurality of lock stops and the rotor defines at least one tooth which is engagable with at least one lock stop when the rotor is in the constrained condition and which does not engage the lock stops when the rotor is in the unconstrained condition.

2. The valve unit of claim 1 wherein the valve member defines at least one port restricting element alignable with the port in a plurality of positions to control flow through the valve unit.

3. The valve unit of claim 1 wherein the valve member is integral with the resilient spring element and is slidable to progressively restrict the port to establish a plurality of flow control settings.

4. The valve unit of claim 1 wherein the rotor includes magnetically attractable elements.

5. The valve unit of claim 4 wherein the rotor includes at least two magnets as the magnetically attractable elements, each magnet having an axis of magnetization that is transverse to the axis of rotation.

6. The valve unit of claim 5 wherein the magnets are spaced on opposite sides of the rotor and each magnet has an axis of magnetization that is arranged to lie between forty-five degrees to ninety degrees relative to the axis of rotation.

7. The valve unit of claim 6 in combination with a setting adjuster tool positionable in proximity with the valve unit, exterior to the patient, and having magnets which have sufficient attractive strength with the magnetically attractable elements to lift the rotor from the constrained condition to the unconstrained condition to enable adjustment of the rotor from an actual setting to another setting.

8. The valve unit of claim 7 wherein the adjuster magnets have at least one axis of magnetization that is alignable substantially in parallel with the axis of rotation of the rotor.

9. The valve unit of claim 8 in combination with a setting indicator tool positionable in proximity with the valve unit, exterior to the patient, and capable of detecting an actual setting of the valve unit without altering the actual setting.

10. The valve unit of claim 9 wherein the indicator tool includes a gear and a wheel which rotates substantially freely in a detection condition when it is disengaged relative to the gear and which is driven to a discrete setting value by the gear in a locked condition.

\* \* \* \* \*